US009708660B2

(12) United States Patent
Fu et al.

(10) Patent No.: US 9,708,660 B2
(45) Date of Patent: *Jul. 18, 2017

(54) USES OF IDED NANOSTRUCTURES IN NUCLEIC ACID TECHNOLOGY

(71) Applicant: NVIGEN, INC., Sunnyvale, CA (US)

(72) Inventors: Aihua Fu, Sunnyvale, CA (US); James Zhu, Cupertino, CA (US)

(73) Assignee: NVIGEN, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/379,494

(22) PCT Filed: Feb. 19, 2013

(86) PCT No.: PCT/US2013/026758
§ 371 (c)(1),
(2) Date: Aug. 19, 2014

(87) PCT Pub. No.: WO2013/123525
PCT Pub. Date: Aug. 22, 2013

(65) Prior Publication Data
US 2015/0031575 A1 Jan. 29, 2015

Related U.S. Application Data

(60) Provisional application No. 61/600,699, filed on Feb. 19, 2012.

(51) Int. Cl.
| C12Q 1/68 | (2006.01) |
| C12M 1/34 | (2006.01) |
| C07H 21/04 | (2006.01) |
| C40B 30/04 | (2006.01) |
| C40B 50/16 | (2006.01) |
| G01N 31/22 | (2006.01) |
| B82Y 15/00 | (2011.01) |
| G01N 21/64 | (2006.01) |

(52) U.S. Cl.
CPC ............ *C12Q 1/6876* (2013.01); *B82Y 15/00* (2013.01); *C12Q 1/6869* (2013.01); *G01N 21/6428* (2013.01)

(58) Field of Classification Search
CPC .......... C12Q 1/68; G01N 21/63; C07H 21/02; B82Y 40/00; C12M 1/34; C40B 30/04
USPC ............ 435/6.1, 6.11, 287.2; 536/23.1, 24.3; 422/430; 506/9, 16, 28, 31; 977/704, 977/773
See application file for complete search history.

(56) References Cited

U.S. PATENT DOCUMENTS

| 6,051,377 A * | 4/2000 | Mandecki | C12Q 1/6825 435/6.19 |
| 7,323,696 B2 * | 1/2008 | Vann | B82Y 5/00 250/458.1 |
| 7,723,662 B2 * | 5/2010 | Levoy | G02B 21/365 250/208.1 |
| 7,932,037 B2 * | 4/2011 | Adler | C12Q 1/6809 435/6.16 |
| 7,955,802 B2 * | 6/2011 | Whitman | C12Q 1/6818 435/6.12 |
| 2003/0232340 A1 | 12/2003 | Anderson | |
| 2003/0232388 A1 * | 12/2003 | Kreimer | B01J 13/0008 435/7.1 |
| 2007/0092870 A1 | 4/2007 | Zhao et al. | |
| 2008/0103296 A1 * | 5/2008 | Zhao | B82Y 5/00 536/22.1 |
| 2009/0179171 A1 | 7/2009 | Sailor | |
| 2009/0203148 A1 * | 8/2009 | Gorfinkel | C12Q 1/6834 436/94 |
| 2010/0008862 A1 * | 1/2010 | Fu | A61K 49/0002 424/9.32 |
| 2010/0137163 A1 | 6/2010 | Link et al. | |
| 2010/0323906 A1 * | 12/2010 | Chen | C12Q 1/6827 506/9 |
| 2011/0267457 A1 | 11/2011 | Weitz et al. | |
| 2011/0311975 A1 * | 12/2011 | Van De Stolpe | C12Q 1/6869 435/6.11 |
| 2012/0021416 A1 | 1/2012 | Zassenhaus | |
| 2013/0210653 A1 * | 8/2013 | Pregibon | C12Q 1/6816 506/9 |
| 2015/0076392 A1 * | 3/2015 | Fu | A61K 49/0002 252/62.51 R |

FOREIGN PATENT DOCUMENTS

WO    WO03/048769 A1    6/2003
WO    WO 2009/047587 A1    4/2009

OTHER PUBLICATIONS

Meade et al, Multiplexed DNA Detection Using Spectrally Encoded Porous SiO2 Photonic Crystal Particles, 2009, Anal. Chem., 81, 2618-2625.*
Rosi Nathaniel L et al: "Nanostructures in biodiagnostics", Chemical Reviews, American Chemical Society, US, vol. 105, No. 4, Apr. 1, 2005 (Apr. 1, 2005), pp. 1547-1562.
Martin G. Bellino et al: "Polymerase-Functionalized Hierarchical Mesoporous Titania Thin Films: Towards a Nanoreactor Platform for DNA Amplifcatino", Small, vol. 6, No. 11, Jun. 6, 2010 (Jun. 6, 2010), pp. 1221-1225.
Han M et al: "Quantum-Dot-Tagged Microbeads for Multiplexed Optical Coding of Biomolecules", Nature biotechnology, Nature Publishing Group, US, vol. 19, No. 7, Jul. 1, 2001 (Jul. 1, 2001), pp. 631-635.

* cited by examiner

*Primary Examiner* — Narayan Bhat
(74) *Attorney, Agent, or Firm* — Jun He Law Offices P.C.; James J. Zhu

(57) ABSTRACT

The present invention relates to compositions comprising a porous nanostructure of a known characteristics and a fragment of nucleic acid having a known sequence. Methods of use of the compositions were also provided, for example in DNA amplification, detection, and DNA sequencing.

12 Claims, 9 Drawing Sheets

| (a) 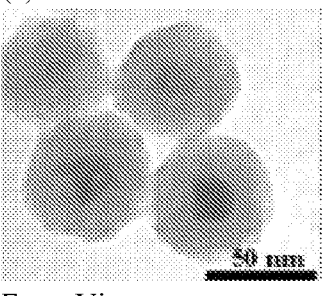 From Viswagen (www.viswagenbiotech.com) product description: TEM of nanoparticles containing magnetic core and silica shell component. This is for their products of magnetic and fluorescent nanoparticles. The silica structure is clearly observable under TEM. | (d) 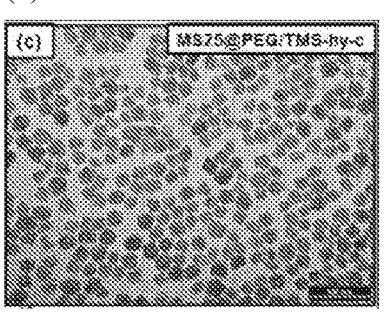 TEM micrograph of mesoporous silica nanoparticles synthesized from prof. Christy L. Hayne's group. The siliceous structure is clearly observable under TEM. (J. Am. Chem. Soc., 2011, 133, 20444-20457.) |
|---|---|
| (b) 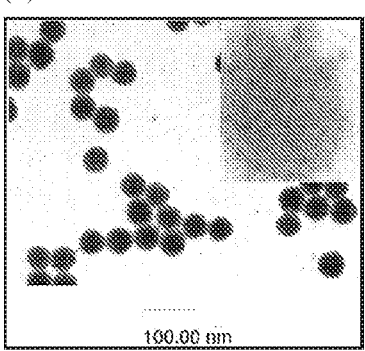 TEM micrograph of luminophore doped silica nanoparticles prepared by Prof. Weihong Tan's group. These silica nanoparticles could be clearly observed under TEM. (Anal. Chem. 2001, 73, 4988-4993.) | (e) 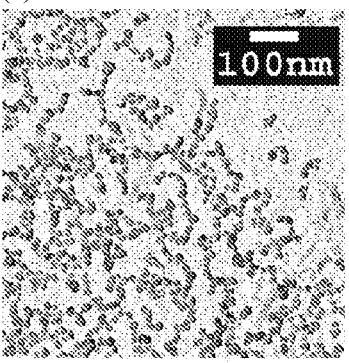 TEM micrograph of fluorescent silica nanoparticles by incorporating organic fluorophores within a siliceous structure from Prof. Ulrich Wiesner's group. the siliceous structure is clearly observable under TEM. (Nano letters, 2005, 5, 113.) |

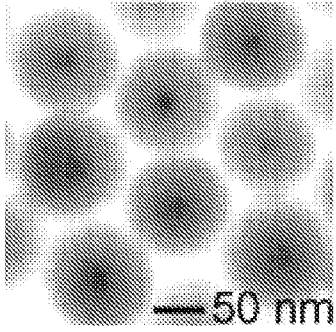

TEM micrograph of core/shell nanoparticles made of iron oxide core and silica shell with fluorescent molecules. The siliceous coating is clearly observable. From prof. Younan Xie's group. (nano letters, 2002, 2, 183.)

(f)

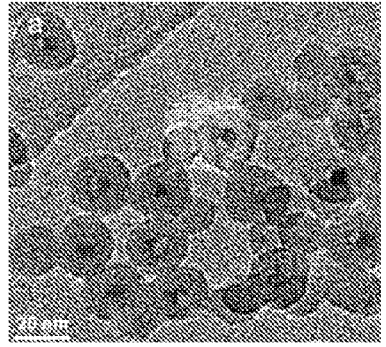

TEM micrograph of silica coated PbSe nanoparticles. The silica coating is clearly observable. From prof. Jackie Ying's group. (Chemistry of Materials, 2007, 19, 3112.)

(f)

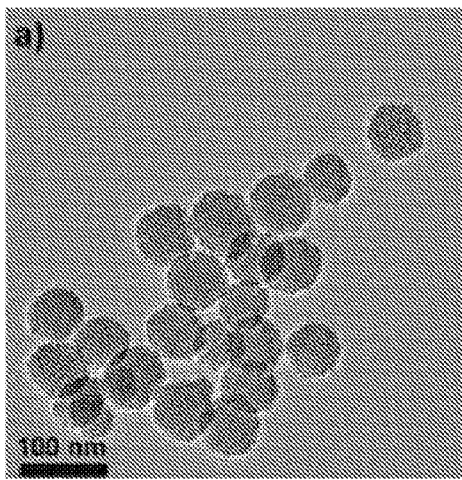

TEM micrograph of silica nanoparticles as synthesized (a) and incorporated with multiple magnetic nanoparticles. The siliceous structure could be clearly observed under TEM. From Dr. Taeghwan Hyeon's group. (JACS, 2010, 132, 552.)

Figure 4 (continued)

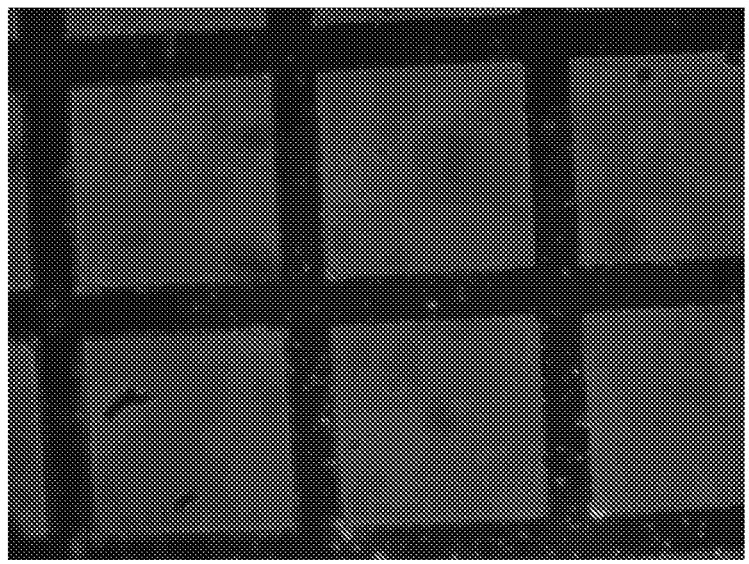
(A)
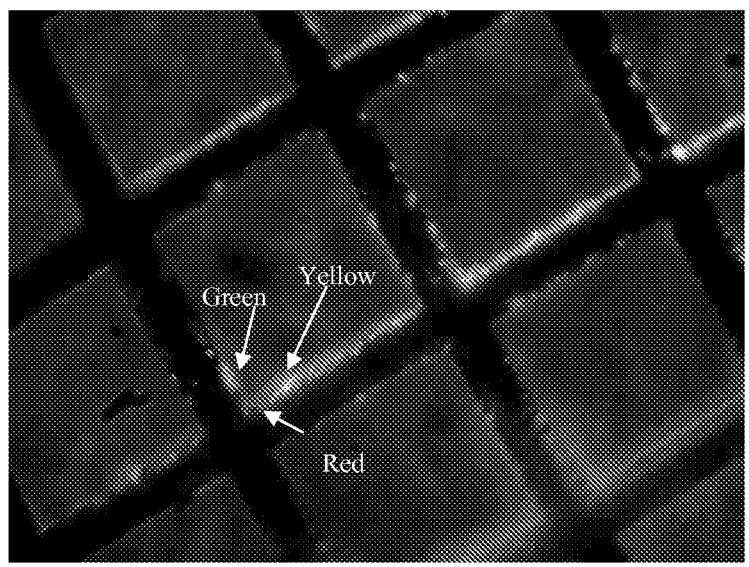
(B)
Figure 12

USES OF IDED NANOSTRUCTURES IN NUCLEIC ACID TECHNOLOGY

CROSS-REFERENCE TO RELATED APPLICATIONS

The present application claims the benefit of U.S. Provisional Patent Application No. 61/600,699, filed on Feb. 19, 2012, which is incorporated herein by reference in its entirety.

FIELD OF THE INVENTION

The present invention is in the field of nucleic acid detection and sequencing.

BACKGROUND

Current DNA detection and sequencing technologies are based primarily on placing DNA targets on substrates such as grids or arrays so that the identities of DNAs are recognized through their location on the substrates. Even in the cases that nanoballs are used in DNA sequencing, these nanoballs are used as carriers for DNA amplification and the amplified DNAs along with nanoballs are still placed on patterned substrates.

Therefore, there are needs in the field to continue to develop new ways for DNA amplification and detection without the necessity of or dependence on substrate. Further, current technology often depends on a limited number of differentiable signals for DNA sequencing, for example, only utilizing 4 different fluorescent colors to code the 4 individual nucleotides, such as in Illumina's sequence by synthesis technology, and in Pacific Biosciences' SMRT technology. Sometimes, the detection signal is only based on one type of signal, for example, the chemiluminescent signal from the pyrosequencing of 454 sequencing technology. These existing technologies only sequence DNA one base by one base, including when the electronic signal is utilized as in the nanopore based sequencing and when the pH change is utilized as in the ion torrent technology. Hence, a method to enable DNA sequencing through longer base steps could be highly beneficial to improve sequencing accuracy, reduce sequencing time, reduce cost, and increase throughput.

SUMMARY OF THE INVENTION

One aspect of the present invention related to compositions comprising a porous nanostructure of a known characteristics and a fragment of nucleic acid having a known sequence.

In certain embodiments, the porous nanostructures have been disclosed in U.S. Prov. Appl. 61/589, 777 (all references cited in the present disclosure are incorporated herein in their entirety). In certain embodiments, the nanostructure comprises at least one core nanoparticle embedded in or coated with a low density porous 3-D structure or coating, which is capable of carrying or associating with at least one payload within or on the surface of the nanostructure.

In certain embodiments, the core nanoparticle comprises a nanoparticle or a cluster of nanoparticles. A single core nanoparticle may comprise a plurality or a cluster of mini-nanoparticles. The nanoparticles in the cluster may be made by the same composition, or different compositions.

In certain embodiments, the core nanoparticle includes, for example, a superparamagnetic iron oxide (SPIO) nanoparticle, or a non-SPIO nanoparticle. The non-SPIO nanparticles include, for example, metallic nanoparticles (e.g., gold or silver nanoparticles), a metal oxide nanoparticle, semiconductor nanoparticle (e.g., quantum dots with individual or multiple components such as CdSe/ZnS, doped heavy metal free quantum dots or other semiconductor quantum dots); polymeric nanoparticles (e.g., particles made of one or a combination of PLGA (poly(lactic-co-glycolic acid), PCL (polycaprolactone), PEG (poly ethylene glycol) or other polymers); siliceous nanoparticles; and non-SPIO magnetic nanoparticles (e.g., $MnFe_2O_4$, SAF, and other types of magnetic nanoparticles). The core nanoparticle has a diameter ranging from about 1 nm to about 900 nm (preferable 1-50 nm, 2-40 nm, 5-20 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm in size).

In certain embodiments, the core nanoparticle has a shape of sphere, rod, tetrapod, pyramidal, multi-armed, nanotube, nanowire, nanofiber, or nanoplate.

In certain embodiments, the low density, porous 3-D structure refers to a structure with density at least 10s times (e.g. 10s times, 20s times, 30s times, 50s times, 70s times, 100s times, 1000s times, 10,000 times) lower than existing mesoporous materials (e.g. mesoporous materials having a pore size ranging from 2 nm to 50 nm). In certain embodiments, the low density, porous 3-D structure has a density of <1.0 g/cc (e.g. from 0.01 mg/cc to 1000 mg/cc). In certain embodiments, the density is determined using dry mass of the 3-D structure divided by the total volume of such 3-D structure in an aqueous solution.

In certain embodiments, the low density, porous 3-D structure is highly porous. Such low density structure further refers to a structure having at least 40% to at least 99.9% (preferably 50% to 99.9%) of empty space or porosity in the structure. In certain embodiments, at least 80% of the pores having size of 1 nm to 500 nm in pore radius.

In certain embodiments, the low density, porous 3-D structure is a structure that can not be obviously observed or substantially invisible under transmission electron microscope, for example, even when the feature size of the low density structure is in the 10s or 100s nanometer range.

In certain embodiments, the low density, porous 3-D structure is made of silicon-containing molecules (e.g., silanes, organosilanes, alkoxysilanes, silicates and derivatives thereof). For example, the silicon-containing molecules can be amino-propyl-trimethoxysilane, mercapto-propyl-trimethoxysilane, carboxyl-propyl-trimethoxysilane, amino-propyl-triethoxysilane, mercapto-propyl-triethoxysilane, carboxyl-propyl-triethoxysilane, Bis-[3-(triethoxysilyl)propyl]-tetrasulfide, Bis-[3-(triethoxysilyl)propyl]-disulfide, aminopropyltriethoxysilane, N-2-(aminoethyl)-3-amino propyltrimethoxysilane, Vinyltrimethoxysilane, Vinyl-tris(2-methoxyethoxy) silane, 3-methacryloxypropyl-trimethoxy silane, 2-(3,4-epoxycyclohexy)-ethyl trimethoxysilane, 3-glycidoxy-propyltriethoxysilane, 3-isocyanatopropyltriethoxysilane, 3-cyanatopropyltriethoxysilane, and sodium silicates.

In certain embodiments, the low density, porous 3-D structure is associated with the core nanoparticle via intra-molecular interaction (e.g. covalent bonds, metallic bonds, and/or ionic bonding) or inter-molecular interaction (e.g. hydrogen bond, and/or non covalent bonds).

In certain embodiments, the low density, porous 3-D structure is a stable crosslinked coating with thickness ranging from 1 nm to 1000 nm (e.g. from 1 nm to 500 nm). In certain embodiments, the thickness of the low density, porous 3-D structure is controllable, so is the number of payloads that could be carried. As a result, the nanostructures when systematically applied as injectable agents into the blood stream of a living subjects can accumulate at a disease region, such as a tumor or inflammation site. In certain embodiments, the nanostructure is capable of carrying or being associated with one or more payloads. In certain embodiments, the payloads to be carried or associated with the nanostructure include, but are not limited to, a detectable agent (e.g. a fluorescent molecule, a chemo-luminescent molecule, a bio-luminescent molecule, a radioisotope, a MRI contrast agent, a CT contrast agent, an enzyme-substrate label, and/or a coloring agent), a targeting moiety (e.g. an antibody, an antigen, a ligand, an aptamer, a peptide, a nucleic acid, a polynucleotide, a polysaccharide, sugar, fatty acid, steroids, pyrimidines, and/or a hapten), a binding partner (e.g. antigen, antibody, receptor, ligand, DNA, RNA, peptide, aptamer, biotin, avidin, streptavidin, lectin, carbohydrate, Protein A, antibody Fc, desthiobiotin, and/or iminobiotin), a biological active agent (e.g. therapeutic agents, proteins, antibodies, peptides, nucleic acids, enzymes, thermal-responsive molecules, optical-responsive molecules, electronic-responsive molecules, magnetic-responsive molecules, pH-responsive molecules, enzymatic responsive molecules and/or chemical compounds), a drug, a therapeutic agent, a radiological agent, a chemological agent, a small molecule drug, a biological drug (e.g., peptides, proteins, antibodies, antigens, nucleic acids, aptamers and the like) and combinations thereof, which can be used to image, detect, study, monitor, evaluate, screen a disease, condition, and/or related biological event. In certain embodiments, the nanostructure comprises a first payload and a second payload.

Another aspect of the present disclosure relates to compositions comprising a first IDed porous nanostructure and a first piece of nucleic acid, wherein the nucleic acid is associated with the IDed porous nanostructure.

In certain embodiments, the nucleic acid is a primer, a probe or a fragment of DNA.

In certain embodiments, the compositions further comprise a magnetic particle,
wherein the magnetic particle is associated with one end of the first nucleic acid and the IDed porous nanostructure is associated with the opposite end of the first nucleic acid.

In certain embodiments, the first nanostructure is magnetic.

In certain embodiments, the compositions further comprise a second IDed porous nanostructure and a second nucleic acid, wherein the second nucleic acid is associated with the second IDed porous nanostructure and complements to said first nucleic acid, and wherein the second IDed nanostructure is not the first nanostructure. In certain embodiments, the second nanostructure is magnetic.

Another aspect of the present disclosure relates to a mixture comprising a first IDed nanostructure and a second IDed nanostructure, wherein the first IDed nanostructure is associated with a first nucleic acid and the second IDed nanostructure is associated with a second nucleic acid. In certain embodiments, the first and second nanostructures are both magnetic. In certain embodiments, the mixture further comprises a third IDed nanostructure, wherein the third IDed nanostructure is associated with a third nucleic acid and complements with the first or second nucleic acids. In certain embodiments, the third nanostructure is magnetic.

Another aspect of the present disclosure relates to methods of detecting a condition in a sample or a subject, comprising: hybridizing a DNA fragment from the sample or the subject with the composition provided herein, and detecting the presence of double stranded DNA in the IDed nanostructure which indicates the presence of a condition in the sample or subject.

Another aspect of the present disclosure relates to methods of detecting a condition in a sample or a subject, comprising: hybridizing a DNA fragment from the sample or the subject with the composition provided herein in a solution, adding a single-stranded endonuclease into the solution, subjecting the solution to a magnetic field, and detecting the presence or coding signal of IDed nanostructure which indicates the presence of a condition in the sample or subject.

Another aspect of the present disclosure relates to methods of detecting the coding signals of a plurality of IDed nanostructures in a solution simultaneously, comprising passing a light from a solution comprising a plurality of IDed nanostructures through a microlens array to a photosensor array, and processing the light data to identify each IDed nanostructure in the solution.

Another aspect of the present disclosure relates to methods of detecting the coding signal of a plurality of IDed nanostructures on a surface, comprising assembling the plurality of IDed nanostructures from a solution onto the surface. In certain embodiments, the assembling is based on chemical interaction, or based on magnetic interaction. In certain embodiments, the IDed nanostructures of the composition are assembled in an ordered array format in the presence of an applied magnetic field.

Another aspect of the present disclosure relates to methods of detecting interaction of a nucleic acid with a testing agent, wherein the nucleic acid is associated with a first IDed porous nanostructure having a first coding signal, and the testing agent is associated with a second IDed porous nanostructure having a second coding signal, comprising: contacting the first IDed porous nanostructure with the second IDed porous nanostructure, and detecting the interaction of the first coding signal and the second coding signal. In certain embodiments, the methods further comprise assembling the first and the second IDed porous nanostructures from a solution to a surface.

Another aspect of the present disclosure relates to methods of forming an amplified DNA sequence, comprising: extending a primer in the presence of both a template DNA and a mixture of IDed nanostructures, wherein each IDed nanostructure is associated with a unique code and a unique combination of two or three consecutive nucleotides.

DESCRIPTION OF THE DRAWINGS

FIG. 4. Exemplary TEM images of coated nanoparticles known in the art, in which the coatings are obviously observable under TEM.

FIG. 12. IDed fluorescent magnetic nanostructures could be spread onto a magnetic grid for identification of DNA hybridization based detection. The IDed fluorescent magnetic nanoparticles were utilized to identify DNA hybridization by examining the nanostructures formed in solution through DNA hybridization connected IDed fluorescent magnetic nanoparticles. These structures are formed in solution, and dispersed onto a 2D surface using a magnetic grid. By flowing the solutions through the magnetic grid, IDed fluorescent magnetic nanoparticles or nanostructures were captured and spread onto the surface for identification. (a) Control experiment: mixture of red and green IDed magnetic nanostructures without DNA oligomers, and accordingly, negligible red and green particle binding together (yellow color) were observed. (b) DNA hybridization results: red and green IDed magnetic nanostructures were conjugated respectively with complementary DNA oligomeric strands, and the nanostructures are more packed together onto the magnetic grid, and yellow color were manifested.

DETAILED DESCRIPTION OF THE INVENTION

Figure 1:
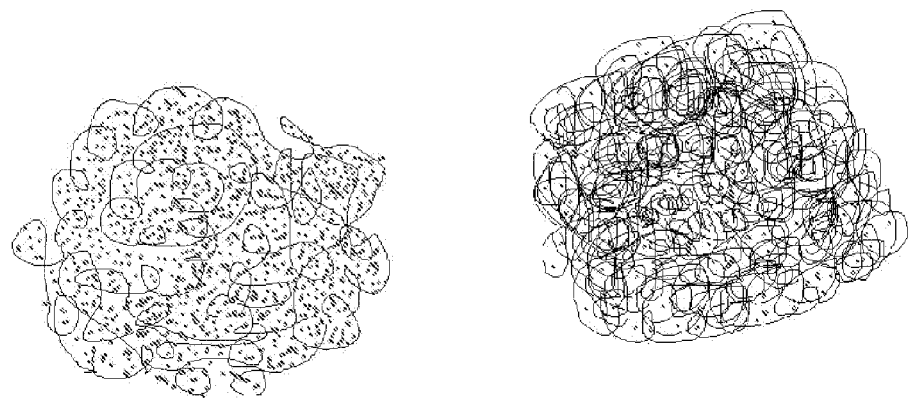
FIG. 1. A schematic comparison of porous nanostructure incorporating a plurality of payloads (dots) with dense nanostructures (black network, right).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, solid state chemistry, inorganic chemistry, organic chemistry, physical chemistry, analytical chemistry, materials chemistry, biochemistry, biology, molecular biology, recombinant DNA techniques, pharmacology, imaging, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

The following embodiments are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for.

It must be noted that, as used in the specification and the appended claims, the singular forms "a," "an," and "the" include plural referents unless the context clearly dictates otherwise. Thus, for example, reference to "a compound"

includes a plurality of compounds. In this specification and in the claims that follow, reference will be made to a number of terms that shall be defined to have the following meanings unless a contrary intention is apparent.

Porous Nanostructures

One aspect of the present disclosure relates to porous nanostructures comprising at least one core nanoparticle embedded in or coated with a low density, porous 3-D structure.

The core nanoparticle used herein includes, but not limited to, a superparamagnetic iron oxide (SPIO) nanoparticle, and a non-SPIO nanoparticle.

The SPIO nanoparticle is an iron oxide nanoparticle, either maghemite ($\gamma$-$Fe_2O_3$) or magnetite ($Fe_3O_4$), or nanoparticles composed of both phases. The SPIO can be synthesized with a suitable method and dispersed as a colloidal solution in organic solvents or water. Methods to synthesize the SPIO nanoparticles are known in the art (see, for example, Morteza Mahmoudi et al, Superparamagnetic Iron Oxide Nanoparticles: Synthesis, Surface Engineering, Cytotoxicity and Biomedical Applications, published by Nova Science Pub Inc, 2011). In one embodiment, the SPIO nanoparticles can be made through wet chemical synthesis methods which involve co-precipitation of $Fe^{2+}$ and $Fe^{3+}$ salts in the presence of an alkaline medium. During the synthesis, nitrogen may be introduced to control oxidation, surfactants and suitable polymers may be added to inhibit agglomeration or control particle size, and/or emulsions (such as water-in-oil microemulsions) may be used to modulate the physical properties of the SPIO nanoparticle (see, for example, Jonathan W. Gunn, The preparation and characterization of superparamagnetic nanoparticles for biomedical imaging and therapeutic application, published by ProQuest, 2008). In another embodiment, the SPIO nanoparticles can be generated by thermal decomposition of iron pentacarbonyl, alone or in combination with transition metal carbonyls, optionally in the presence of one or more surfactants (e.g. lauric acid and oleic acid) and/or oxidatants (e.g. trimethylamine-N-oxide), and in a suitable solvent (e.g. dioctyl ether or hexadecane) (see, for example, US patent application 20060093555). In another embodiment, the SPIO nanoparticles can also be made through gas deposition methods, which involves laser vaporization of iron in a helium atmosphere containing different concentrations of oxygen (see, Miller J. S. et al., Magnetism: Nanosized magnetic materials, published by Wiley-VCH, 2002).

In certain embodiments, the SPIO nanoparticles are those disclosed in US patent application US20100008862.

The non-SPIO nanoparticles include, for example, metallic nanoparticles (e.g., gold or silver nanoparticles (see, e.g., Hiroki Hiramatsu, F. E. O., Chemistry of Materials 16, 2509-2511 (2004)), semiconductor nanoparticles (e.g., quantum dots with individual or multiple components such as CdSe/ZnS (see, e.g., M. Bruchez, et al., Science 281, 2013-2016 (1998))), doped heavy metal free quantum dots (see, e.g., Narayan Pradhan et al, J. Am. chem. Soc. 129, 3339-3347 (2007)) or other semiconductor quantum dots); polymeric nanoparticles (e.g., particles made of one or a combination of PLGA (poly(lactic-co-glycolic acid) (see, e.g., Minsoung Rhee et al., Adv. Mater. 23, H79-H83 (2011)), PCL (polycaprolactone) (see, e.g., Marianne Labet et al., Chem. Soc. Rev. 38, 3484-3504 (2009)), PEG (poly ethylene glycol) or other polymers); siliceous nanoparticles; and non-SPIO magnetic nanoparticles (e.g., $MnFe_2O_4$ (see, e.g., Jae-Hyun Lee et al., Nature Medicine 13, 95-99 (2006)), synthetic antiferromagnetic nanoparticles (SAF) (see, e.g., A. Fu et al., Angew. Chem. Int. Ed. 48, 1620-1624 (2009)), and other types of magnetic nanoparticles).

The non-SPIO nanoparticles can be prepared or synthesized using suitable methods known in the art, such as for example, sol-gel synthesis method, water-in-oil micro-emulsion method, gas deposition method and so on. For example, gold nanoparticles can be made by reduction of chloroaurate solutions (e.g. $HAuCl_4$) by a reducing agent such as citrate, or acetone dicarboxylate. For another example, CdS semiconductor nanoparticle can be prepared from $Cd(ClO_4)_2$ and $Na_2S$ on the surface of silica particles. For another example, II-VI semiconductor nanoparticles can be synthesized based on pyrolysis of organometallic reagents such as dimethyl cadmium and trioctylphosphine selenide, after injection into a hot coordinating solvent (see, e.g. Günter Schmid, Nanoparticles: From Theory to Application, published by John Wiley & Sons, 2011). Doped heavy metal free quantum dots, for example Mn-doped ZnSe quantum dots can be prepared using nucleation-doping strategy, in which small-sized MnSe nanoclusters are formed as the core and ZnSe layers are overcoated on the core under high temperatures. For another example, polymeric nanoparticles can be prepared by emulsifying a polymer in a two-phase solvent system, inducing nanosized polymer droplets by sonication or homogenization, and evaporating the organic solvent to obtain the nanoparticles. For another example, siliceous nanoparticles can be prepared by sol-gel synthesis, in which silicon alkoxide precursors (e.g. TMOS or TEOS) are hydrolyzed in a mixture of water and ethanol in the presence of an acid or a base catalyst, the hydrolyzed monomers are condensed with vigorous stirring and the resulting silica nanoparticles can be collected. For another example, SAFs, a non-SPIO magnetic nanoparticle, can be prepared by depositing a ferromagenetic layer on each of the two sides of a nonmagnetic space layer (e.g. ruthenium metal), along with a chemical etchable copper release layer and protective tantalum surface layers, using ion-bean deposition in a high vacuum, and the SAF nanoparticle can be released after removing the protective layer and selective etching of copper.

The size of the core nanoparticles ranges from 1 nm to 100 nm in size (preferable 1-50 nm, 2-40 nm, 5-20 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm in size). The size of nanoparticles can be controlled by selecting appropriate synthesis methods and/or systems. For example, to control the size of nanoparticles, synthesis of nanoparticles can be carried out in a polar solvent which provides ionic species that can adsorb on the surface of the nanoparticles, thereby providing electrostatic effect and particle-particle repulsive force to help stabilize the nanoparticles and inhibit the growth of the nanoparticles. For another example, nanoparticles can be synthesized in a micro-heterogeneous system that allows compartmentalization of nanoparticles in constrained cavities or domains. Such a micro-heterogeneous system may include, liquid crystals, mono and multilayers, direct micelles, reversed micelles, microemulsions and vesicles. To obtain nanoparticles within a desired size range, the synthesis conditions may be properly controlled or varied to provide for, e.g., a desired solution concentration or a desired cavity range (a detailed review can be found at, e.g. Vincenzo Liveri, Controlled synthesis of nanoparticles in microheterogeneous systems, Published by Springer, 2006).

The shape of the core nanoparticles can be spherical, cubic, rod shaped (see, e.g., A. Fu et al., Nano Letters, 7, 179-182 (2007)), tetrapo-shaped (see, e.g., L. Manna et al.,

*Nature Materials*, 2, 382-385 (2003)), pyramidal, multi-armed, nanotube, nanowire, nanofiber, nanoplate, or any other suitable shapes. Methods are known in the art to control the shape of the nanoparticles during the preparation (see, e.g. Waseda Y. et al., Morphology control of materials and nanoparticles: advanced materials processing and characterization, published by Springer, 2004). For example, when the nanoparticles are prepared by the bottom-up process (i.e. from molecule to nanoparticle), a shape controller which adsorbs strongly to a specific crystal plane may be added to control the growth rate of the particle.

A single core nanoparticle may comprise a single nanoparticle or a plurality or a cluster of mini-nanoparticles (A. Fu et al., *J. Am. Chem. Soc.* 126, 10832-10833 (2004), J. Ge et al., *Angew. Chem. Int. Ed.* 46, 4342-4345 (2007), Zhenda Lu et al., *Nano Letters* 11, 3404-3412 (2011).). The mini-nanoparticles can be homogeneous (e.g., made of the same composition/materials or having same size) or heterogeneous (e.g., made of different compositions/materials or having different sizes). A cluster of homogeneous mini-nanoparticles refers to a pool of particles having substantially the same features or characteristics or consisting of substantially the same materials. A cluster of heterogeneous mini-nanoparticles refers to a pool of particles having different features or characteristics or consisting of substantially different materials. For example, a heterogeneous mini-nanoparticle may comprise a quantum dot in the center and a discrete number of gold (Au) nanocrystals attached to the quantum dot. Different nanoparticles in a heterogeneous nanoparticle pool do not need to associate with each other at first, but rather, they could be individually and separately associated with the low density porous structure.

In certain embodiments, a nanostructure disclosed comprising a plurality of core nanoparticles embedded in or coated with a low density, porous 3-D structure. For example, the nanostructure contains 2, 3, 4, 5, 6, 7, 8, 9, 10, 11, 12, 13, 14, 15, 16, 17, 18, 19, 20, 25, 30, 35, 40, 50, 60, 70, 80, 90, 100, 100s or 1000s core nanoparticles.

In certain embodiments, the low density, porous 3-D structure refers to a structure with density much lower (e.g. 10s times, 20s times, 30s times, 50s times, 70s times, 100s times) than existing mesoporous nanoparticles (e.g. mesoporous nanoparticles having a pore size ranging from 2 nm to 50 nm). (A. Vincent, et. al., J. Phys. Chem. C, 2007, 111, 8291-8298. J. E. Lee, et. al., J. Am. Chem. Soc., 2010, 132, 552-557. Y. S. Lin, et. al., J. Am. Chem. Soc., 2011, 133, 20444-20457. Z. Lu, Angew. Chem. Int. Ed., 2010, 49, 1862-1866.)

In certain embodiments, the low density, porous 3-D structure refers to a structure having a density of <1.0 g/cc (e.g., <100 mg/cc, <10 mg/cc, <5 mg/cc, <1 mg/cc, <0.5 mg/cc, <0.4 mg/cc, <0.3 mg/cc, <0.2 mg/cc, or <0.1 mg/cc) (for example, from 0.01 mg/cc to 10 mg/cc, from 0.01 mg/cc to 8 mg/cc, from 0.01 mg/cc to 5 mg/cc, from 0.01 mg/cc to 3 mg/cc, from 0.01 mg/cc to 1 mg/cc, from 0.01 mg/cc to 1 mg/cc, from 0.01 mg/cc to 0.8 mg/cc, from 0.01 mg/cc to 0.5 mg/cc, from 0.01 mg/cc to 0.3 mg/cc, from 0.01 mg/cc to 1000 mg/cc, from 0.01 mg/cc to 915 mg/cc, from 0.01 mg/cc to 900 mg/cc, from 0.01 mg/cc to 800 mg/cc, from 0.01 mg/cc to 700 mg/cc, from 0.01 mg/cc to 600 mg/cc, from 0.01 mg/cc to 500 mg/cc, from 0.1 mg/cc to 800 mg/cc, from 0.1 mg/cc to 700 mg/cc, from 0.1 mg/cc to 1000 mg/cc, from 1 mg/cc to 1000 mg/cc, from 5 mg/cc to 1000 mg/cc, from 10 mg/cc to 1000 mg/cc, from 20 mg/cc to 1000 mg/cc, from 30 mg/cc to 1000 mg/cc, from 30 mg/cc to 1000 mg/cc, from 30 mg/cc to 900 mg/cc, from 30 mg/cc to 800 mg/cc, or from 30 mg/cc to 700 mg/cc).

The density of 3-D structure can be determined using various methods known in the art (see, e.g., Lowell, S. et al., Characterization of porous solids and powders: surface area, pore size and density, published by Springer, 2004). Exemplary methods include, Brunauer Emmett Teller (BET) method and helium pycnometry (see, e.g., Varadan V. K. et al., Nanoscience and Nanotechnology in Engineering, published by World Scientific, 2010). Briefly, in BET method, dry powders of the testing 3-D structure is placed in a testing chamber to which helium and nitrogen gas are fed, and the change in temperature is recorded and the results are analyzed and extrapolated to calculate the density of the testing sample. In helium pycnometry method, dry powders of the testing 3-D structure are filled with helium, and the helium pressure produced by a variation of volume is studied to provide for the density. The measured density based on the dry power samples does not reflect the real density of the 3-D structure because of the ultralow density of the 3-D structure, the framework easily collapses during the drying process, hence providing much smaller numbers in the porosity measurement than when the 3-D structure is fully extended, for example, like when the 3-D structure is fully extended in a buffer solution.

In certain embodiments, the density of the 3-D structure can be determined using the dry mass of the 3-D structure divided by the total volume of such 3-D structure in an aqueous solution. For example, dry mass of the core particles with and without the 3-D structure can be determined respectively, and the difference between the two would be the total mass of the 3-D structure. Similarly, the volume of a core particle with and without the 3-D structure in an aqueous solution can be determined respectively, and the difference between the two would be the volume of the 3-D structure on the core particle in an aqueous solution.

In certain embodiments, the porous nanostructure can be dispersed as multiple large nanoparticles coated with the 3-D structure in an aqueous solution, in such case, the total volume of the 3-D structure can be calculated as the average volume of the 3-D structure for an individual large nanoparticle multiplied with the number of the large nanoparticles.

For each individual large nanoparticle, the size (e.g. radius) of the particle with 3-D structure can be determined with Dynamic Light Scattering (DLS) techniques, and the size (e.g. radius) of the particle core without the 3-D structure can be determined under Transmission Electron Microscope (TEM), as the 3-D structure is substantially invisible under TEM. Accordingly, the volume of the 3-D structure on an individual large nanoparticle can be obtained by subtracting the volume of the particle without 3-D structure from the volume of the particle with the 3-D structure.

The number of large nanoparticles for a given core mass can be calculated using any suitable methods. For example, an individual large nanoparticle may be composed of a plurality of small nanoparticles which are visible under TEM. In such case, the average size and volume of a small nanoparticle can be determined based on measurements under TEM, and the average mass of a small nanoparticle can be determined by multiplying the known density of the core material with the volume of the small particle. By dividing the core mass with the average mass of a small nanoparticle, the total number of small nanoparticles can be estimated. For an individual large nanoparticle, the average number of small nanoparticles in it can be determined under TEM. Accordingly, the number of large nanoparticles for a given core mass can be estimated by dividing the total number of small nanoparticles with the average number of small nanopariticels in an individual large nanoparticle.

Alternatively, the low density, porous 3-D structure refers to a structure having 40%-99.9% (preferably 50% to 99.9%) of empty space or pores in the structure, where 80% of the pores having size of 1 nm to 500 nm in pore radius.

The porosity of the 3-D structure can be characterized by the Gas/Vapor adsorption method. In this technique, usually nitrogen, at its boiling point, is adsorbed on the solid sample. The amount of gas adsorbed at a particular partial pressure could be used to calculate the specific surface area of the material through the Brunauer, Emmit and Teller (BET) nitrogen adsorption/desorption equation. The pore sizes are calculated by the Kelvin equation or the modified Kelvin equation, the BJH equation (see, e.g. D. Niu et al., *J. Am. Chem. Soc.* 132, 15144-15147 (2010)).

The porosity of the 3-D structure can also be characterized by mercury porosimetry (see, e.g. Varadan V. K. et al., supra). Briefly, gas is evacuated from the 3-D structure, and then the structure is immersed in mercury. As mercury is non-wetting at room temperature, an external pressure is applied to gradually force mercury into the sample. By monitoring the incremental volume of mercury intruded for each applied pressure, the pore size can be calculated based on the Washburn equation.

Figure 2:
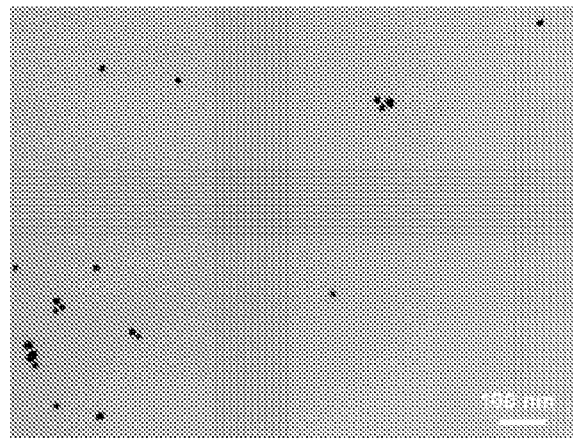
FIG. 2. An exemplary TEM image of silanized Au nanoparticles with core size of Au at ~20 nm and hydrodynamic size ~60 nm. No siliceous coating is visible from the TEM.
Figure 3:
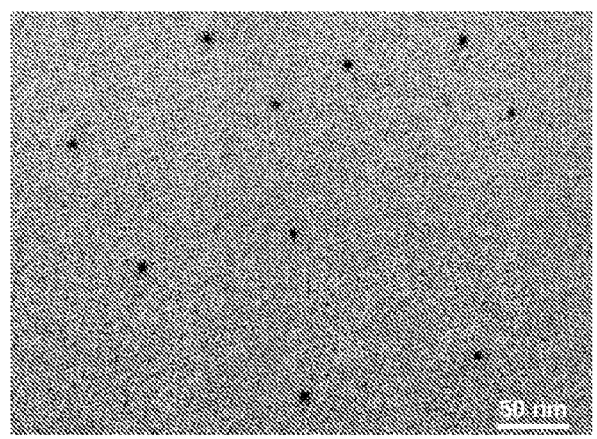
FIG. 3. An exemplary TEM image of silanized quantum dots with nanoparticle core size of ~6 nm and hydrodynamic size ~200 nm. The siliceous coating is not obviously visible from the TEM.

Alternatively, the low density, porous 3-D structure refers to a structure that has a material property, that is, the porous structure (except to the core nanoparticle or core nanoparticles) could not be obviously observed or substantially transparent under transmission electron microscope, for example, even when the feature size of the 3-D structure is in the 10s or 100s nanometer range. The term "obviously observed" or "substantially transparent" as used herein means that, the thickness of the 3-D structure can be readily estimated or determined based on the image of the 3-D structure under TEM. The nanostructure (e.g. nanoparticles coated with or embedded in/on a low density porous 3-D structure) can be observed or measured by ways known in the art. For example, the size (e.g. radius) of the nanostructure with the 3-D structure can be measured using DLS methods, and the size (e.g. radius) of the core particle without the 3-D structure can be measured under TEM. In certain embodiments, the thickness of the 3-D structure is measured as 10s, 100s nanometer range by DLS, but cannot be readily determined under TEM. For example, when the nanostructures provided herein are observed under Transmission Electron Microscope (TEM), the nanoparticles can be identified, however, the low density porous 3-D structure can not be obviously observed, or is almost transparent (e.g., see FIGS. 2 and 3). This distinguishes the nanostructures provided herein from those reported in the art (see, FIG. 4) that comprise nanoparticles coated with crosslinked and size tunable 3-D structure, including the mesoporous silica nanoparticles or coating (see, e.g., J. Kim, et. al., J. Am. Chem. Soc., 2006, 128, 688-689; J. Kim, et. al., Angew. Chem. Int. Ed., 2008, 47, 8438-8441). This feature also indicates that the low density porous 3-D structure provided herein has a much lower density and/or is highly porous in comparison to other coated nanoparticles known in the art.

The porosity of the 3-D structure can be further evaluated by the capacity to load different molecules (see, e.g. Wang L. et al., *Nano Research* 1, 99-115 (2008)). As the 3-D structure provided herein has a low density, it is envisaged that more payload can be associated with the 3-D structure than with other coated nanoparticles (see, e.g. FIG. 1). For example, when 3-D structure is loaded with organic fluorophores such as Rhodamin, over $10^5$ Rhodamin molecules can be loaded to 3-D structure of one nanoparticle.

In certain embodiments, the low density structure refers to a structure capable of absorbing or carrying a fluorescent payload whose fluorescence intensity is at least 100 fold of that of the free fluorescent molecule (e.g. at least 150 fold, 200 fold, 250 fold, 300 fold, 350 fold, 400 fold, 450 fold, 500 fold, 550 fold or 600 fold). The fluorescence intensity of a loaded nanoparticle can be quantified under the same excitation and emission wave lengths as that of the fluorescent molecules. The fluorescence intensity of the loaded low density structure indicates the payload of the fluorescent molecule, and also indirectly reflects the porosity of the low density structure.

In certain embodiments, the low density, porous 3-D structure is made of silane-containing or silane-like molecules (e.g., silanes, organosilanes, alkoxysilanes, silicates and derivatives thereof).

In certain embodiments, the silane-containing molecule comprises an organosilane, which is also known as silane coupling agent. Organosilane has a general formula of $R_xSiY_{(4-x)}$, wherein R group is an alkyl, aryl or organofunctional group. Y group is a methoxy, ethoxy or acetoxy group. x is 1, 2 or 3. The R group could render a specific function such as to associate the organosilane molecule with the surface of the core nanoparticle or other payloads through covalent or non-covalent interactions. The Y group is hydrolysable and capable of forming a siloxane bond to crosslink with another organosilane molecule. Exemplary R groups include, without limitation, disulphidealkyl, aminoalkyl, mercaptoalkyl, vinylalkyl, epoxyalkyl, and methacrylalkyl, carboxylalkyl groups. The alkyl group in an R group can be methylene, ethylene, propylene, and etc. Exemplary Y groups include, without limitation, alkoxyl such as $OCH_3$, $OC_2H_5$, and $OC_2H_4OCH_3$. For example, the organosilane can be amino-propyl-trimethoxysilane, mercapto-propyl-trimethoxysilane, carboxyl-propyl-trimethoxysilane, amino-propyl-triethoxysilane, mercapto-propyl-triethoxysilane, carboxyl-propyl-triethoxysilane, Bis[3-(triethoxysilyl) propyl]-tetrasulfide, Bis[3-(triethoxysilyl) propyl]-disulfide, aminopropyltriethoxysilane, N-2-(aminoethyl)-3-amino propyltrimethoxysilane, Vinyltrimethoxysilane, Vinyl-tris (2-methoxyethoxy) silane, 3-methacryloxypropyltrimethoxy silane, 2-(3,4-epoxycyclohexy)-ethyl trimethoxysilane, 3-glycidoxy-propyltriethoxysilane, 3-isocyanatopropyltriethoxysilane, and 3-cyanatopropyltriethoxysilane.

The 3-D structure interacts with the core nanoparticles through 1) intra-molecular interaction such as covalent bonds (e.g., Sigma bond, Pi bond, Delta bond, Double bond, Triple bond, Quadruple bond, Quintuple bond, Sextuple bond, 3c-2e,3c-4-e,4c-2e, Agostic bond, Bent bond, Dipolar bond, Pi backbond, Conjugation, Hyperconjugation, Aromaticity, Hapticity, and Antibonding), metallic bonds (e.g., chelating interactions with the metal atom in the core nanoparticle), or ionic bonding (cation π-bond and salt bond), and 2) inter-molecular interaction such as hydrogen bond (e.g., Dihydrogen bond, Dihydrogen complex, Low-barrier hydrogen bond, Symmetric hydrogen bond) and non covalent bonds (e.g., hydrophobic, hydrophilic, charge-charge, or 7r-stacking interactions, van der Waals force, London dispersion force, Mechanical bond, Halogen bond, Aurophilicity, Intercalation, Stacking, Entropic force, and chemical polarity).

Methods for Preparing the Porous Nanostructure

Another aspect of the present disclosure relates to methods of forming a nanostructure comprising at least one core nanoparticle with low-density, porous 3-D structure. For example, the nanostructure is formed by coating or surrounding one or more core nanoparticle with low density, porous 3-D structure such that the particle(s) is or are embedded in the 3-D structure.

The low-density, porous 3-D structure is formed by the depositing, or covering of the surface of the core nanoparticle through the assembly or cross-linking of silane-containing or silane-like molecules. The low density porous 3-D structure can be prepared by a silanization process on the surface of the core nanoparticles. Silanization process includes, for example, the steps of crosslinking silicon-containing or silane-like molecules (e.g., alkoxysilanes such as amino-propyl-trimethoxysilane, mercapto-propyl-trimethoxysilane, or sodium silicate) under acidic or basic conditions.

In certain embodiments, an acidic or a basic catalyst is used in the crosslinking. Exemplary acid catalyst include, without limitation, a protonic acid catalyst (e.g. nitric acid, acetic acid and sulphonic acids) and Lewis acid catalyst (e.g. boron trifluoride, boron trifluoride monoethylamine complex, boron trifluoride methanol complex, $FeCl_3$, $AlCl_3$, $ZnCl_2$, and $ZnBr_2$). Exemplary basic catalysts include, an amine or a quaternary ammonium compound such as tetramethyl ammonium hydroxide and ammonia hydroxide.

The silanization process may include one or more stages, for example, a priming stage in which the 3-D structure starts to form, a growth stage in which a layer of siliceous structure is readily formed on the core nanoparticle and more are to be formed, and/or an ending stage in which the 3-D structure is about to be completed (e.g. the outer surface of the 3-D structure is about to be formed). During the silanization process, one or more silane-containing molecules can be added at different stages of the process. For example, in the priming stage, organosilanes such as amino-propyl trimethoxyl silane or mercaptopropyl trimethoxyl silane can be added to initiate the silanization on the core nanoparticle surface. For another example, silane molecules having fewer alkoxy group (e.g. only 2 alkoxy group) can be added to the reaction at the growth stage of silanization. For another example, at the ending stage of silanization, organo silane molecules with one or a variety of different functional groups may be added. These functional groups can be amino, carboxyl, mercapto, or phosphonate group, which can be further conjugated with other molecules, e.g. hydrophilic agent, a biologically active agent, a detectable label, an optical responsive group, electronic responsive group, magnetic responsive group, enzymatic responsive group or pH responsive group, or a binding partner, so as to allow further modification of the 3-D structure in terms of stability, solubility, biological compatibility, capability of being further conjugation or derivation, or affinity to payload. Alternatively, the functional groups can also be a group readily conjugated with other molecules (e.g. a group conjugated with biologically active agent, a thermal responsive molecule, an optical responsive molecule, an electronic responsive molecule, a magnetic responsive molecule, a pH responsive molecule, an enzymatic responsive molecule, a detectable label, or a binding partner such as biotin or avidin).

To control the formation of low density siliceous structure, the preparation further includes density reducing procedures such as introducing air bubbles in the reaction or formation, increasing reaction temperature, microwaving, sonicating, vertexing, labquakering, and/or adjusting the chemical composition of the reaction to adjust the degree of the crosslinking of the silane molecules. Without being bound to theory, it is believed that these procedures can help make the reaction medium homogeneous, well dispersed and promote the formation of low density porous 3-D structure with increased voids or porosity.

In certain embodiments, the density reducing procedure comprises sonicating the reaction or formation mixture. The conditions of the sonicating procedure (e.g. duration) in the silanization process can be properly selected to produce a desired porosity in the resulting low density porous 3-D structure. For example, the sonicating can be applied throughout a certain stage of the silanization process. The duration of sonicating in a silanization stage may last for, e.g. at least 1 hour, 1.5 hours, 2 hours, 2.5 hours, 3 hours, 3.5 hours, 4 hours. In certain embodiments, sonicating is applied in each stage of the silanization process.

In certain embodiments, the density reducing procedures comprise introducing at least one alcohol to the reaction. In certain embodiments, the alcohol has at least 3 (e.g. at least 4, at least 5 or at least 6) carbon atoms. For example, the alcohol may have 3, 4, 5, 6, 7, 8, 9, 10, 11, 12 or more carbon atoms. In certain embodiments, the alcohol can be monohydric alcohols, or polyhydric alcohols. Illustrative examples of monohydric alcohols include, propanol, butanol, pentanol, hexyl alcohol, etc. Illustrative examples of polyhydric alcohols include, propylene glycol, glycerol, threitol, xylitol, etc. In certain embodiments, the alcohol can have a saturated carbon chain or an unsaturated carbon chain. An alcohol having a saturated carbon chain can be represented as $C_nH_{(2n+2)}O$ in chemical formula. In certain embodiments, n is no less than 3, or no less than 4, or no less than 5 (e.g. n=3, 4, 5, 6, 7, 8, 9, 10, 11, 12 or more). Alcohol with an unsaturated carbon chain has a double or a triple bond between two carbon atoms. In certain embodiments, the alcohol can be a cyclic alcohol, for example, cyclohexanol, inositol, or menthol.

In certain embodiments, the alcohol can have a straight carbon chain (e.g. n-propyl alcohol, n-butyl alcohol, n-pentyl alcohol, n-hexyl alcohol, etc) or a branched carbon chain (e.g. isopropyl alcohol, isobutyl alcohol, tert-butyl alcohol, etc). In certain embodiments, the alcohol is present in a volume fraction of about 30% to about 70% (e.g. about 30% to about 70%, about 30% to about 60%, about 30% to about 55%, about 40% to about 70%, about 45% to about 70%, about 40% to about 60%). In certain embodiments, the alcohol is present in volume fraction of around 50% (e.g. around 45%, around 46%, around 47%, around 48%, around 49%, around 50%, around 51%, around 52%, around 53%, around 54%, around 55%, around 56%, around 57%, around 58%, around 59%, or around 60%,).

In certain embodiments, the density reducing procedure comprises introducing air bubbles to the reaction. In certain embodiments, the air bubbles can be in constant presence during the reaction process. The air bubbles can be introduced to the reaction through any suitable methods, for example, by blowing bubbles to the reaction, or by introducing a gas-producing agent to the reaction mixture.

Other experimental conditions can also be optimized to provide for formation of a desired low density porous 3-D structure. Such experimental conditions include, for example, the concentration of the core nanoparticles, the concentration of the catalyst, the ratio of the concentration of the catalyst and the core nanoparticle, the temperature at which the low density siliceous structure is formed, or the molecular structure of the organosilanes.

In certain embodiments, the method further comprises introducing one or more functional groups within in or on the surface of the porous structure. The functional groups may be introduced during the formation of the porous structure during the cross-linking process, for example, by adding silicon-containing compounds containing such functional groups during the cross-linking, in particular, during the ending stage of the cross-linking process. The functional groups may also be introduced after the formation of the cross-linking product, for example, by introducing functional groups to the surface of the cross-linking product by chemical modification. In certain embodiments, the functional groups are inherent in the porous structure.

The functional groups serve as linkage between the porous structure and payloads. Examples of the functional groups include, but are not limited to amino, mercapto, carboxyl, phosphonate, biotin, streptavidin, avidin, hydroxyl, alkyl or other hydrophobic molecules, polyethylene glycol or other hydrophilic molecules, and photo cleavable, thermo cleavable or pH responsive linkers.

In certain embodiments, the method further comprises purifying the obtained nanostructure product. The purification may include use of dialysis, tangential flow filtration, diafiltration, or combinations thereof.

The thickness of the low density porous 3-D structure, which directly correlates to the size of the nanostructure, could be controlled (e.g. from 1 nm to 1000 nm) by, for example, modifying the quantity of the silane-containing molecules (e.g. trialkoxysilane or sodium silicate), the reaction time, and time lapse between reaction steps and such kind of reaction parameters.

The thickness of the 3-D structure can be about 1 to 5 nm thick. In certain embodiments, the thickness can be about 1 to 10 nm thick. In certain embodiments, the thickness can be about 1 to 20 nm thick. In certain embodiments, the thickness can be about 1 to 30 nm thick. In certain embodiments, the thickness can be about 1 to 40 nm thick. In certain embodiments, the thickness can be about 1 to 50 nm thick. In certain embodiments, the thickness can be about 1 to 60 nm thick. In certain embodiments, the thickness can be about 1 to 100 nm thick. In certain embodiments, the thickness can be about 1 to 500 nm thick. In certain embodiments, the thickness can be about 1 to 1000 nm thick.

After the low-density, porous 3-D structure is formed on the surface of the core nanoparticle, the core nanoparticle is embedded in the 3-D structure. The resulting nanostructure can have a thickness (e.g., the longest dimension of the nanostructure or a diameter if the structure is a sphere) of about 1 to 1000 nm, 1 to 100 nm, or 1 to 10 nm. In another embodiment, the nanostructure can have a diameter of about 1 to 30 nm. In another embodiment, the nanostructure can have a diameter of about 500 nm. In another embodiment, the nanostructure can have a diameter of about 100 nm. In another embodiment, the nanostructure can have a diameter of about 50 nm. In another embodiment, the nanostructure can have a diameter of about 30 nm. In another embodiment, the nanostructure can have a diameter of about 10 nm.

Payloads

In certain embodiments, the nanostructures provided herein carry or are associated with a payload. The payloads to be carried or associated with the nanostructure include, but are not limited to, a detectable agent, a targeting moiety, a binding partner, a biological active agent, a drug, a therapeutic agent, a radiological agent, a chemological agent, a small molecule drug, a biological drug (e.g., peptides, proteins, antibodies, antigens, nucleic acids, aptamers, and the like) and combinations thereof, which can be used to image, detect, study, monitor, evaluate, screen, and/or a disease, condition, or related biological event. Payloads may be physically absorbed into the porous structure or linked to the porous structure through functional groups disclosed herein.

A detectable agent can be a fluorescent molecule, a chemo-luminescent molecule, a bio-luminescent molecule, a radioisotope, a MRI contrast agent, a CT contrast agent, an enzyme-substrate label, and/or a coloring agent etc. Examples of fluorescent molecules include, without limitation, fluorescent compounds (fluorophores) which can include, but are not limited to: 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AFPs—AutoFluorescent Protein—(Quantum Biotechnologies); Alexa® Fluor 350; Alexa® Fluor 405; Alexa® Fluor 500; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; Bimane; Bisbenzamide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson™; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; Chlorophyll; Chromomycin A; Chromomycin A; CL-NERF; CMFDA; Coumarin Phalloidin; C-phycocyanine; CPM Methylcoumarin; CTC; CTC Formazan; Cy2™; Cy3.18; Cy3.5™; Cy3™; Cy5.18; Cy5.5™; Cy5™; Cy7™; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3' DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DID S; Dihydrorhodamine 123 (DHR); DiI (DiIC18(3)); Dinitrophenol;

DiO (DiOC18(3)); DiR; DiR (DiIC18(7)); DM-NERF (high pH); DNP; Dopamine; DTAF; DY-630-NHS; DY-635-NHS; ELF 97; Eosin; Erythrosin; Erythrosin ITC; Ethidium Bromide; Ethidium homodimer-1 (EthD-1); Euchrysin; Euko-Light; Europium (III) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow SGF; GeneBlazer (CCF$_2$); Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf; JC-1; JO-JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PYMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); S65A; S65C; S65L; S65T; SBFI; Serotonin; Sevron Brilliant Red 2B; Sevron Brilliant Red 4G; Sevron Brilliant Red B; Sevron Orange; Sevron Yellow L; SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodaminelsoThioCyanate; True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; YOYO-3, Sybr Green, Thiazole orange (interchelating dyes), fluorescent semiconductor nanoparticles, lanthanides or combinations thereof.

Examples of radioisotopes include, $^{123}$I, $^{124}$I, $^{125}$I, $^{131}$I, $^{35}$S, $^{3}$H, $^{111}$In, $^{112}$In, $^{14}$C, $^{64}$Cu, $^{67}$Cu, $^{86}$Y, $^{88}$Y, $^{90}$Y, $^{177}$Lu, $^{211}$At, $^{186}$Re, $^{188}$Re, $^{153}$Sm, $^{212}$Bi, $^{32}$P, $^{18}$F, $^{201}$Tl, $^{67}$Ga, $^{137}$Cs and other radioisotopes.

Examples of enzyme-substrate labels include, luciferases (e.g., firefly luciferase and bacterial luciferase), luciferin, 2,3-dihydrophthalazinedionesm, alate dehydrogenase, urease, peroxidase such as horseradish peroxidase (HRPO), alkaline phosphatase, -galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

A targeting moiety has affinity to an interested target (e.g., a cell, a cellular component, a tissue, a protein, an antibody, an antigen, a DNA, a RNA and the like). Examples of a targeting moiety include, antibodies (e.g. antibodies to tumor surface antigens, antibodies to cell-specific antigens, or antibodies to receptors), a ligand to a receptor (e.g. growth factors, hormones, cytokines, or neurotransmitters), aptamers, peptides, antigens, nucleic acids, polynucleotides, polysaccharides, sugars, fatty acids, steroids, purines, pyrimidines, a hapten or combinations thereof.

Examples of a binding partner include, antibodies, antigens, receptors, ligands, DNA, RNA, peptide, aptamer, biotin, avidin, strepavidin, lectin, carbohydrate, Protein A, antibody Fc, desthiobiotin, and iminobiotin.

Examples of a biologically active agent include, therapeutic agents, proteins, antibodies, peptides, nucleic acids, enzymes, thermal-responsive molecules, optical-responsive molecules, electronic-responsive molecules, magnetic-responsive molecules, pH-responsive molecules, enzymatic responsive molecules and/or chemical compounds. Exemplary of therapeutic agents include, without limitation, local anesthetics, antiepileptic drugs and anticonvulsants, anti-alzheimer's disease drugs, analgesics, antipodaghc, anti-hypertensive drugs, antiarrhythmic drugs, diuretic drugs, drugs for treating liver diseases, drugs for treating pancreatic diseases, antihistamine drugs, anti-allergic drugs, glucocorticoid drugs, sex hormone drugs and contraceptive drugs, hypoglycemic drugs, anti-osteoporosis drugs, antibiotics, sulfonamides, quinolones, and other synthetic antibacterial drugs, antituberculous drugs, antiviral drugs, anti-neoplasm drugs, and immunomodulators.

With respect to antigens or antibodies thereof, a protein of interest can be any one or more of the following antigens including but not limited to: 1) leukocyte markers, such as CD2, CD3, CD4, CD5, CD6, CD7, CD8, CD11a,b,c, CD13, CD14, CD18, CD19, CD20, CD22, CD23, CD27 and its ligand, CD28 and its ligands B7.1, B7.2, B7.3, CD29 and its ligand, CD30 and its ligand, CD40 and its ligand gp39, CD44, CD45 and isoforms, CDw52 (Campath antigen), CD56, CD58, CD69, CD72, CTLA-4, LFA-1 and TCR; 2)

histocompatibility antigens, such as MHC class I or II, the Lewis Y antigens, SLex, SLey, SLea, and SLeb; 3) integrins, such as VLA-1, VLA-2, VLA-3, VLA-4, VLA-5, VLA-6, and LFA-1; 4) adhesion molecules, such as Mac-1 and p150, 95; 5) selectins, such as L-selectin, P-selectin, and E-selectin and their counterreceptors VCAM-1, ICAM-1, ICAM-2, and LFA-3; 6) interleukins, such as IL-1, IL-2, IL-3, IL-4, IL-5, IL-6, IL-7, IL-8, IL-10, IL-11, IL-12, IL-13, IL-14; and IL-15; 7) interleukin receptors, such as IL-1R, IL-2R, IL-4R, IL-5R, IL-6R, IL-7R, IL-8R, IL-10R, IL-11R, IL-12R, IL-13R, IL-14R, and IL-15R; 8) chemokines, such as PF4, RANTES, MIP1.alpha., MCP1, NAP-2, Grou, Grog, and IL-8; 9) growth factors, such as TNFalpha, TGFbeta, TSH, VEGF/VPF, PTHrP, EGF family, FGF, PDGF family, endothelin, and gastrin releasing peptide (GRP); 10) growth factor receptors, such as TNFalphaR, RGFbetaR, TSHR, VEGFR/VPFR, FGFR, EGFR, PTHrPR, PDGFR family, EPO-R, GCSF-R and other hematopoietic receptors; 11) interferon receptors, such as IFN.alpha.R, IFN.beta.R, and IFN.gamma.R; 12) Igs and their receptors, such as IgE, FceRI, and FCeR11; 13) tumor antigens, such as her2-neu, mucin, CEA and endosialin; 14) allergens, such as house dust mite antigen, lol pl (grass) antigens, and urushiol; 15) viral proteins, such as CMV glycoproteins B, H, and gCIII, HIV-1 envelope glycoproteins, RSV envelope glycoproteins, HSV envelope glycoproteins, EBV envelope glycoproteins, VZV envelope glycoproteins, HPV envelope glycoproteins, Hepatitis family surface antigens; 16) toxins, such as pseudomonas endotoxin and osteopontin/uropontin, snake venom, and bee venom; 17) blood factors, such as complement C3b, complement C5a, complement C5b-9, Rh factor, fibrinogen, fibrin, and myelin associated growth inhibitor; 18) enzymes, such as cholesterol ester transfer protein, membrane bound matrix metalloproteases, and glutamic acid decarboxylase (GAD); and 19) miscellaneous antigens including ganglioside GD3, ganglioside GM2, LMP1, LMP2, eosinophil major basic protein, eosinophil cationic protein, PANCA, Amadori protein, Type IV collagen, glycated lipids, .gamma.-interferon, A7, P-glycoprotein and Fas (AFO-1) and oxidized-LDL.

In certain embodiments, a protein of interest can be antibodies or fragments thereof which bind to an antigen (non-limiting example of antigens are shown as above). The antibodies or fragments can be polyclonal, monoclonal, of animal origin (e.g., murine, rabbit, camel), of human origin (e.g., fully human), chimeric, humanized, variable regions, CDRs, ScFv, bispecific, diabody, or other forms of antibodies with antigen-binding capabilities.

The payload may be introduced during or after the formation of the nanostructures. For example, when the nanostructure is formed through silanization process, the payload (e.g. a fluorescent compound) can be introduced to the silanization system, so as to allow the incorporation of the payload into the nanostructure during the silanization process. For another example, the payload may be mixed with the readily formed nanostructure, e.g. in solution, dispersion, suspension, emulsion etc, to allow incorporation of the payload to the porous compartment of the nanostructure, or to allow conjugation of the payload to the functional groups on the nanostructure.

In certain embodiment, at least one payload can be associated with the porous structure. For example, only one group of homogenous payloads are associated with the porous structure. For another example, the first payload and the second payload are associated with the porous structure. While both payloads are selected from the groups consisting of a detectable agent, a targeting moiety, a binding partner, a biological active agent, a drug, a therapeutic agent, a radiological agent, a chemological agent, a small molecule drug, a biological drug (e.g., peptides, proteins, antibodies, antigens, nucleic acids, aptamers, and the like); the first payload is not the same as the second payload. For instance, the first payload is a targeting agent that lead the nanostructure to specifically binds to or be associated with a target (e.g., a cancer cell), and the second payload is a detectable gent (for diagnosis) or a therapeutic agent (for treatment).

In certain embodiments, the first payload is associated with the porous structure in one area of the structure and the second payload is associated with the porous structure in another area of the structure so that the nanostructure can be directional or oriented with respect to the distribution of payloads in the nanostructure. Such site selective modification could be achieved by depositing the porous structure on a substrate, then partially coating the substrate with a protective polymer layer, such as poly(3-hexyl-thiophene) (P3HT) and poly(methyl methacrylate) that could be dissolved using certain solvents such as chloroform or pyridine after the site selective modification is finished. (Liu H., et. al., nano letters, 2004, vol 4., 2397-2401). A second modification could be achieved after the protective layer is removed and the unmodified nanostructure is exposed and further modified with different payloads. Further, the nanostructure could be deposited on the substrate with bonding through cleavable molecules, for example, photo cleavable molecules such as photocleavable biotin amine reactive labeling reagents (www.ambergen.com), then the nanostructure could be released after site selective modifications. In addition, with cleavable linker molecule bound to the substrate, the nanostructures could be released after the first site selective modification (SSM1). SSM1 could include both functional groups for linking the SSM1 modified area to a substrate in the next site selective modification step and payloads for signal generating, drugs or other functional purposes. The procedure could be repeated for SSM2. By controlling the protective polymer layer thickness, 3rd, 4th or more site selective modification steps could be carried out to render the nanostructures multiple regions of different payloads.

Products by Process

Another aspect of the present disclosure relates to nanostructures prepared by any of the methods provided herein. The nanostructures prepared herein may be optionally isolated, purified, dried, or associated with one or more payloads, using methods described herein and/or conventional methods known in the art. The nanostructures prepared in the present disclosure can be further characterized for the 3-D structure, such as density, porosity, surface areas, thickness etc. of the 3-D structure. Optionally, the payloads may be characterized as well, such as the amount of the payload or the detectable signal of the payload.

IDed Nanostructures

Another aspect of the present disclosure relates to compositions comprising a porous nanostructure of a known characteristics and a fragment of nucleic acid having a known sequence. In certain embodiments, the porous nanostructures have been disclosed in U.S. Prov. Appl. 61/589, 777 (all references cited in the present disclosure are incorporated herein in their entirety). In certain embodiments, the porous nanostructure has the characteristics as disclosed herein.

In certain embodiments, the present disclosure provides a composition comprising a first IDed porous nanostructure and a first piece of nucleic acid, wherein the nucleic acid is associated with the IDed porous nanostructure. The term "IDed" as used herein, means that the porous nanostructure is associated with a known code or a known label that allows identification of the porous nanostructure. "Code" as used herein, refers to a molecule capable of generating a detectable signal that distinguishes one IDed porous nanostructure from another.

The characteristics or the identity of a given nanostructure can be based on multiplexed optical coding system as disclosed in Han et al., Nature Biotechnology, Vol. 19, pp: 631-635 (2001) or U.S. patent application Ser. No. 10/185,226. Briefly, multicolor semiconductor quantum-dots (QDs) are embedded in the porous nanostructure. For each QD, there is a given intensity (within the levels of, for example. 0-10) and a given color (wavelength). For each single color coding, the porous nanostructure has different intensity of QDs depending on the number of QDs embedded therein. If QDs of multiple colors (n colors) and multiple intensity (m levels of intensity) are used, then the porous nanostructures may have a total number of unique identities or codes, which is equal to m to the exponent of m less one ($m^n-1$). In addition, since the porous structure can be associated with additional payloads (e.g., fluorescent organic molecules), if there are Y number of additional fluorescent colors available, the total number of code can be $Y \times (m^n-1)$.

Figure 9:
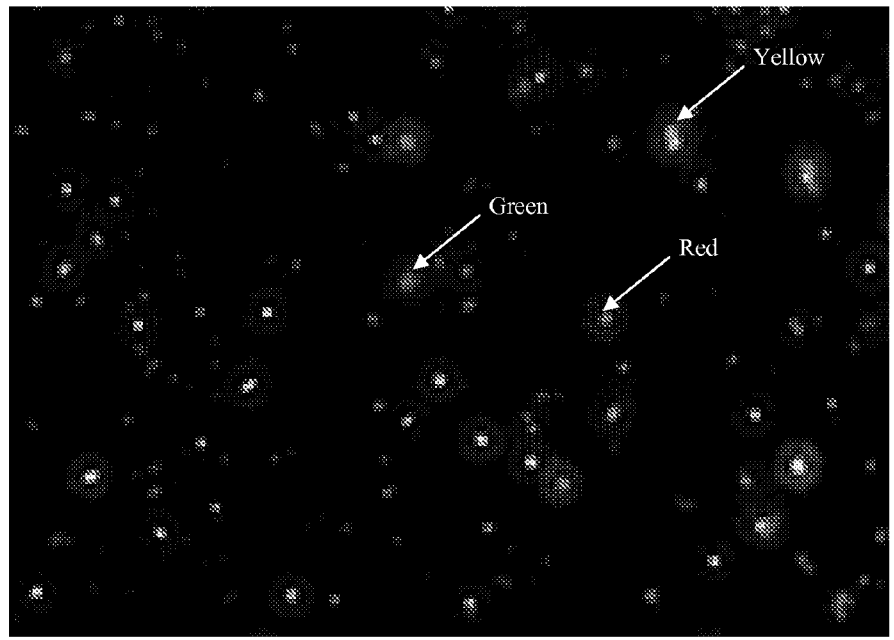
FIG. 9. An image of IDed nanostructures under fluorescent microscope. The IDed nanostructures were incorporated with different fluorescent molecules, showing red, green and yellow colors.

Alternatively or additionally, the identity of a given IDed porous nanostructure can be based on the fluorescent payload associated therewith. Fluorescent payloads of different colors can be embedded in the porous nanostructures, thereby generating different IDed porous nanostructures coded by different fluorescent colors or signals (see, for example, FIG. 9).

In certain embodiments, the IDed porous nanostructure has magnetic property. Magnetic property can facilitate manipulation (e.g. separation or delivery) of the nanostructures using magnetic interaction. Magnetic IDed porous nanostructures can comprise one or a cluster of SIPO nanoparticles as core nanoparticles. The magnetic IDed nanostructures can be attracted to or magnetically guided to a target site when subject to a strong magnetic field, for example a magnetic field from high-filed and/or high-gradient magnets. For example, a magnet (e.g. magnetic grid) can be placed in the proximity of the nanostructures so as to attract the magnetic nano structures.

In certain embodiments, an IDed porous nanostructure is associated with at least one piece of nucleic acid. The fragment of a nucleic acid can be associated with the IDed porous nanostructure in non-covalent interactions (e.g. hydrogen bonds, ionic bonds, etc) or covalent interactions. In certain embodiments, the nucleic acid is associated to one or more functional groups on the IDed porous nanostructure. Any functional groups as disclosed herein can be used (e.g. amino, carboxyl, mercapto, phosphonate group, biotin, streptavidin, avidin, hydroxyl, alkyl or other molecules, linkers or groups). In certain embodiments, the nucleic acid is associated with the IDed porous nanostructure through streptavidin-biotin interactions. For example, the IDed porous nanostructure has streptavidin on its surface, and the nucleic acid is conjugated with biotin. After combining the two, streptavidin strongly binds to avidin and thereby associating the IDed porous nanostructure with the fragment of the nucleic acid. In certain embodiments, the present disclosure further provides an IDed porous nanostructure capable of be associated with a nucleic acid, through one or more functional groups (e.g. streptavidin, biotin, amino, carboxyl, mercapto, phosphonate group, etc.) on the IDed porous nanostructure. The piece of the nucleic acid can be in a suitable length, for example, at least 5, 6, 7, 8, 9, 10, 11, 12, 13, 14, 15, 16, 17, 18, 19, 20, 25, 30, 40, 50, 60, 70, 80, 90, 100 or more bases.

In certain embodiments, the IDed porous nanostructure is associated with a fragment of a nucleic acid with a known sequence. The nucleic acid can be a primer or a sequence probe or a fragment for detection.

In certain embodiments, the IDed porous nanostructure associated with a nucleic acid has magnetic property.

In certain embodiments, the compositions further comprise a second IDed porous nanostructure and a second nucleic acid, wherein the second nucleic acid is associated with the second IDed porous nanostructure and complements to said first nucleic acid, and wherein the second IDed nanostructure is not the first nanostructure. The first and the second IDed porous nanostructure can have different coding signals, so that they can be distinguished from each other when separated. The first and the second nucleic acids can hybridize to each other and thereby allowing association between the first and the second IDed porous nanostructures.

In certain embodiments, the first nucleic acid may be a probe of known sequence and the second nucleic acid may be a sample nucleic acid. If the sample nucleic acid binds to the probe, then the first and the second IDed nanostructures can be associated as manifested by the co-localization of the coding signals of the first and the second nanostructures. Accordingly, association of the first and the second IDed nanostructure indicates that the sample nucleic acid hybridizes to the probe sequence or comprises a complement of the probe sequence.

Either of the first and the second IDed porous nanostructures can be magnetic. A magnetic field can be applied to allow separation of the associated products of the first and the second IDed nanostructures. The separated products can be further observed for both coding signals, and presence of both signals in co-localization indicates association.

Another aspect of the present disclosure relates to a mixture comprising a first IDed nanostructure and a second IDed nanostructure, wherein the first IDed nanostructure is associated with a first nucleic acid and the second IDed nanostructure is associated with a second nucleic acid. In certain embodiments, the first and second nanostructures are both magnetic. In certain embodiments, the mixture further comprises a third IDed nanostructure, wherein the third IDed nanostructure is associated with a third nucleic acid and complements with the first or second nucleic acids. In certain embodiments, the third nanostructure is magnetic.

A plurality of probes of known sequences can be each associated with a different IDed nanostructure, such that one ID corresponds to one probe. A sample nucleic acid can be associated with a further IDed nanostructure, and then be mixed with the plurality of probes on the IDed nanostructures. If the sample nucleic acid hybridizes with any of the probes, the corresponding coding signals of the IDed nanostructures can be detected in association with each other. In this way, the sample nucleic acid can be screened against different probes in one reaction. In certain embodiments, any or all of the IDed nanostructures can be magnetic. For example, the IDed nanostructure associated with the sample nucleic acid can be magnetic. After the hybridization reaction, the sample nucleic acid can be separated through magnetic interaction, and coding signals can be detected to identify the probe(s) that hybridize with the sample nucleic acid.

In certain embodiments, the capture probes or polynucleotide concatemers disclosed in U.S. Pat. No. 7,910,354 can be deposited or linked or associated to the IDed porous nanostructures and used to form amplified DNA clusters.

Figures 5, 6:
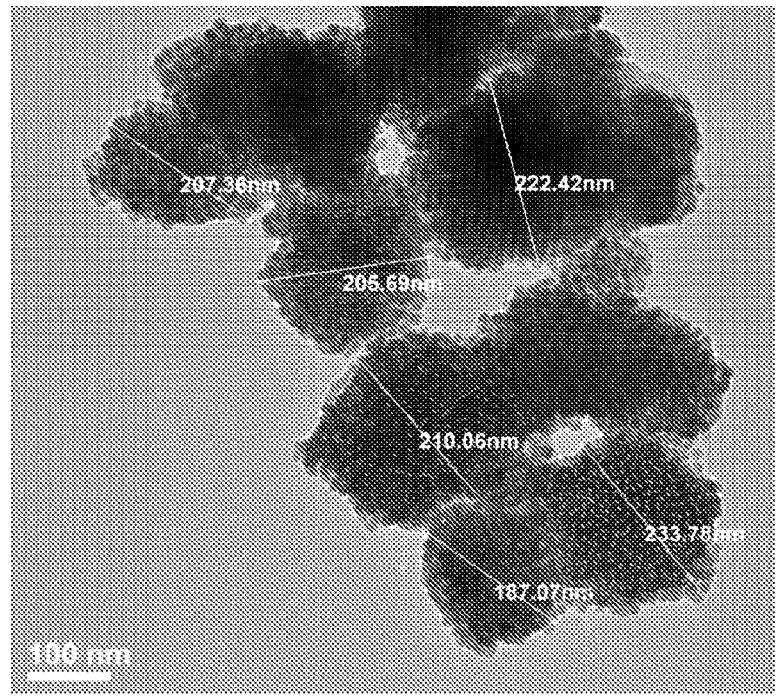
FIG. 5. An exemplary TEM image of porous nanostructure, in which the diameters of the large core nanoparicles are shown.
FIG. 6. Illustration of the DNA coding for 1 nucleotide each sequencing step (left) compared with 2 nucleotides each sequencing step.
Figure 7:
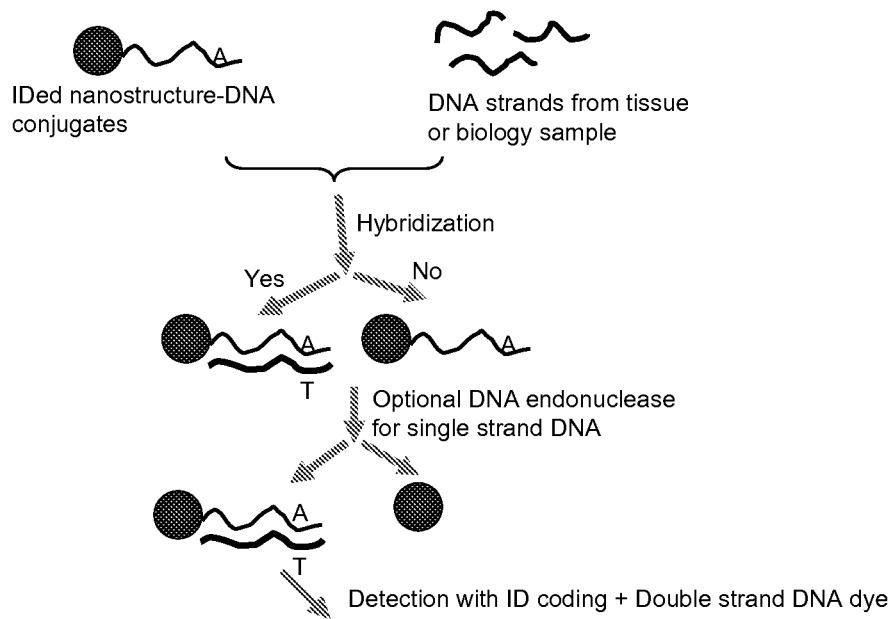
FIG. 7. Illustration to utilize IDed nanostructures to detect DNA fragments from tissue or biological samples.

In certain embodiments, the probe can be associated or linked with the IDed nanostructure. In conventional technologies, a set of four fluorescent colors are used to represent the change of a single nucleotide (See FIG. 6, Current Technology, F—fluoresce). In the present disclosure, since the nanostructures can be associated with a total number of $Y(m^n-1)$ codes, probes having exponentiation of four can be made and used in, for example, sequencing. As shown in FIG. 6, for two consecutive nucleotides to be detected, sixteen (4×4) IDed nanostructures can be associated with each probe and each can be detected based on their coding (N—IDed nanostructure). By the same token, three consecutive nucleotides can be detected by using 64 different coded, IDed nanostructures. For Z number of consecutive nucleotides to be detected, e different IDed nanostructures can be used, as far as $4^Z < Y \times (m^n-1)$. In certain embodiment, a known fragment of nucleotide is associated or linked with an IDed nanostructure. As shown in FIG. 7, a fragment of DNA with mutation is associated with the IDed nanostructures and contacted with DNA fragments from a subject or a sample (e.g., cells or tissues or organs). The hybridized solution can further be treated with single stranded DNA endonucleases (e.g., S1 endonuclease). The mixture solution is further treated with a double stranded DNA dye. The detection of the presence of double stranded DNA on a known IDed nanostructure indicates the presence of DNAs in the subject or sample, and therefore, a condition associated with the DNA (e.g., SNPs or a disease condition). In detection of the presence of double stranded DNA the sample can be assayed in a temperature that denature double stranded DNA and in a second temperature that stabilized double stranded DNA, the different emission indicates the presence of double stranded DNA in the IDed nanostructure.

Figure 8:
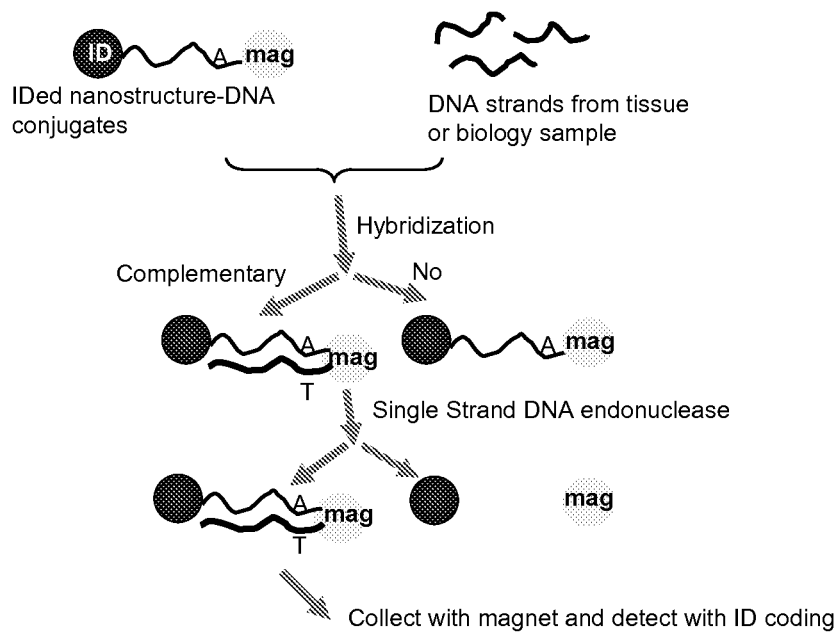
FIG. 8. Illustration to utilize magnetic IDed nanostructure to detect DNA fragments from tissue or biological samples.

In certain embodiments, the IDed porous nanostructure associated with a piece of nucleic acid further comprises a magnetic particle, and the magnetic particle is associated with one end of the nucleic acid and the IDed porous nanostructure is associated with the other end of the nucleic acid. The magnetic particle can facilitate manipulation of the nucleic acid, and the IDed porous nanostructure can provide for detection or identification of the nucleic acid. Such a differently conjugated nucleic acid can be prepared using suitable methods. In certain embodiments, each end of the nucleic acid can have a different functional group which allows selective conjugation of the IDed porous nanostructure or the magnetic particle. In certain embodiments, one end of the nucleic acid is protected when the other end is being conjugated, and then deprotected for a further conjugation. As shown in FIG. 8, a probe fragment (single strand) is linked to an IDed nanostructure and a magnetic particle (e.g., magnetic nanostructure) on both ends and is hybridized with fragments from a subject or a sample. The hybridization mixture is then subject to endonuclease specific to single stranded DNA. If the probe fragment is hybridized to a fragment from the sample, the complex is intact in the presence of the nuclease. If no hybridization occurs, the probe fragment is cleaved and the IDed nanostructure is separated from the magnetic particle. The mixture is then subject to a magnetic field. The IDed nanostructures are detected (if there is hybridization) and the coding signal(s) indicates the presence of a target DNA which corresponds to a condition in the subject or the sample. If there is no hybridization, then only the magnetic particles associated with no IDed nanostructure are pulled down and no coding can be detected.

In certain embodiments, a plurality of primers or probes can be associated with a single IDed nanostructure. For example, an IDed nanostructure carries a pair of primers and is subject to polymerase chain reaction (PCR). The presence of amplicon (e.g., via double stranded DNA dye) can be detected and quantified. If multiple IDed nanostructures (each has a pair of primer) are used in a PCR mixture, then a multiplex real-time PCR can be performed, the presence and the quantification of each amplicon can be detected.

The term "double stranded DNA dye" used herein refers to a fluorescent dye that (1) is related to a fragment of DNA and (2) emits at a different wavelength in the presence of double stranded form from the presence of single stranded form. The dye increases its emission in the presence of double stranded DNA and decreases its emission when duplex DNA unwinds. Examples include, but are not limited to, ethidium bromide, YO-PRO-1, Hoechst 33258, SYBR Gold, and SYBR Green I. A double stranded DNA intercalating dye is not covalently linked to a primer or a nucleic acid template. Ethidium bromide is a fluorescent chemical that intercalates between base pairs in a double stranded DNA fragment and is commonly used to detect DNA following gel electrophoresis. When excited by ultraviolet light between 254 nm and 366 nm, it emits fluorescent light at 590 nm. The DNA-ethidium bromide complex produces about 50 times more fluorescence than ethidium bromide in the presence of single stranded DNA. SYBR Green I is excited at 497 nm and emits at 520 nm. The fluorescence intensity of SYBR Green I increases over 100 fold upon binding to double stranded DNA against single stranded DNA. An alternative to SYBR Green I is SYBR Gold introduced by Molecular Probes Inc. Similar to SYBR Green I, the fluorescence emission of SYBR Gold enhances in the presence of DNA in duplex and decreases when double stranded DNA unwinds. However, SYBR Gold's excitation peak is at 495 nm and the emission peak is at 537 nm. SYBR Gold reportedly appears more stable than SYBR Green I. Hoechst 33258 is a known bisbenzimide double stranded DNA dye that binds to the AT rich regions of DNA in duplex. Hoechst 33258 excites at 350 nm and emits at 450 nm. YO-PRO-1, exciting at 450 nm and emitting at 550 nm, has been reported to be a double stranded DNA specific dye. In a preferred embodiment of the present invention, the double stranded DNA dye is SYBR Green I.

Figure 10:
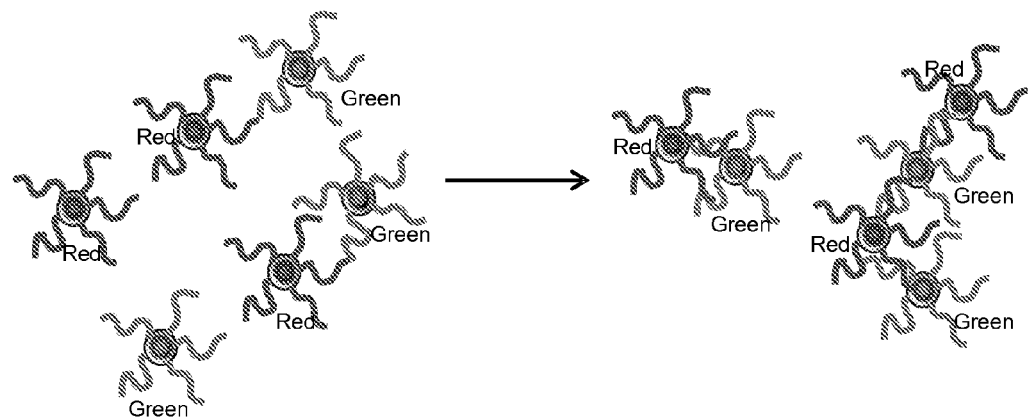
FIG. 10. Illustration to utilize IDed nanostructures to detect hybridization of DNA strands. For IDed nanostructures, the ID and the DNA strands on the particle could be paired up. The ID signal directly corresponds to a specific DNA sequence. For example, if red and green IDed nanostructures bind together through the DNA hybridization, the known sequence of the DNA on red particle could be used to derive/detect DNA sequence on green particles.

In certain embodiments, a probe can be associated with a first IDed nanostructure, and a sample nucleic acid can be associated with a second nanostructure. As shown in FIG. 10, the first and the second IDed nanostructures are different in codes, e.g. one is red and the other is green. The first probe-IDed nanostructure and the second sample-IDed nanostructure are mixed to allow hybridization. If the probe and the sample nucleic acid hybridize with each other, then the association or co-localization of the first and the second IDed nanostructures can be detected.

Figure 13:
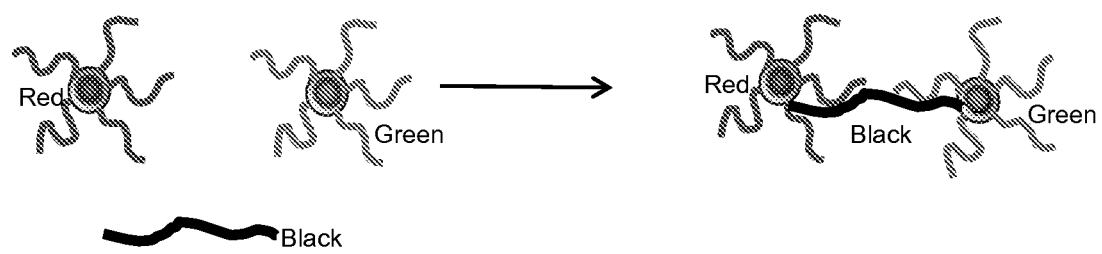
FIG. 13. Illustration to utilize IDed magnetic nanostructures to detect hybridization of a first DNA strand and a second DNA strand with a third DNA strand, in which the first DNA strand hybridizes to the first portion of the third DNA strand, and the second DNA strand hybridizes to the second portion of the third DNA strand.

In certain embodiments, a first probe can be associated with a first IDed nanostructure, and a second probe can be associated with a second IDed nanostructure, where the first probe and the second probe are capable of hybridizing to a respective portion of a sample nucleic acid (e.g. the first probe hybridizes to the first half of the sample, and the second probe hybridizes to the second half of the sample). As shown in FIG. 13, the first and the second IDed nanostructures are different in coding signals, e.g. one is red and the other is green. If the sample nucleic acid is present, then both the first and the second probes would be associated with the sample nucleic acid, thereby resulting in detection of association or co-localization of the first and the second IDed nanostructures.

In certain embodiments, the present disclosure further provides a mixture comprising a first IDed nanostructure and a second IDed nanostructure, wherein the first IDed nanostructure has a first coding signal and the second IDed nanostructure has a second coding signal. In certain embodimens, the first IDed nanostructure has magnetic property while the second IDed nanostructure has not.

Methods of Detection and/or Use

In certain embodiments, a single or a plurality of IDed nanostructures as disclosed herein can be used and detected at the same time, preferably in mixture or solution. The IDed nanostructure associated with nucleic acid, primers, probes, or fragments can be detected.

Another aspect of the present disclosure relates to methods of detecting the coding signals of a plurality of IDed nanostructures in a solution simultaneously, comprising passing a light from a solution comprising a plurality of IDed nanostructures through a microlens array to a photosensor array, and processing the light data to identify each IDed nanostructure in the solution. The methods can be used to detect the coding signals (the intensity and color) of a nanostructure or a plurality of nanostructure in solution (without the needs for array or substrate) at the same time or in real time. For example, as disclosed in U.S. Pat. No. 7,936,392, light sources passing through the solution containing a plurality of IDed nanostructure and the value of passing through light is detected by photosensors. Light data is then collected through an imaging arrangement and processed to facilitate focusing and optical correction via software. As a result, the information about the IDed nanostructures (e.g., the color and intensity) are recoded by passing the light through once without the need for focusing image on each focal plane. The same image computation is also used in microscope. Under the microscopic setting, the solution is imaged by passing light from a microlens array to a photosensor array to simultaneously detect light from the solution which is passed through different directions to different locations. The light data is then analyzed to gain datasets for all IDed nanostructures in the solution in the single shot (For detailed information, see U.S. Pat. No. 7,723,662).

Another aspect of the present invention relates to a method of detecting the coding signals of a plurality of IDed nanostructures on a surface by assembling the IDed nanostructures from the solution onto the surface. The assemble can be based on chemical interaction, for example, forming of a covalent binding between the IDed nanostructure and the corresponding functional groups on the surface, or biological interaction, for example, biotin-streptavidin interaction, by making functional arrays of appropriate biomolecules on the surface. The assemble can also be based on magnetic interaction. For example the IDed nanostructures can be associated with a magnetic particle which can be attracted in response to an applied magnetic field. The IDed nanostructure could also be assembled onto a surface in an ordered array format using the interactions between the magnetic content of the IDed nanostructure and a magnetizable or magnetic grid. The assembling of the IDed nanostructures from solution to a surface can greatly improve or facilitate the detection and/or quantification of the IDed nanostructures. For example, assemble of the IDed nanostructures on a surface allows imaging and observation of the IDed nanostructures on one field under a microscope, in contrast, IDed nanostructures scattered in a solution can be difficult to image or quantify under a microscope.

Another aspect of the present invention related to the detection of coding signals of IDed nanostructures. Although it is not necessary to place the IDed nanostructures onto substrate (e.g., solution based detection as disclosed herein), the IDed nanostructures can be placed onto a substrate, in the same fashion DNA nanoballs or other conventional nanoparticles can be placed onto a substrate and detection occurs after the IDed nanostructures are on the substrate. In certain embodiments, the IDed nanostructures can be distributed onto a magnetic substrate (e.g., a magnetic grid).

Another aspect of the present disclosure relates to methods of forming an amplified DNA sequence, comprising extending a primer in the presence of both a template DNA and a mixture of IDed nanostructures, wherein each IDed nanostructure is associated with a unique code and a unique combination of two or three consecutive nucleotides. As shown in FIG. 6, a set of IDed nanostructures can be used and each represents a unique combination of nucleotides. By paring with the template DNA, the primer is extended with the combination of nucleotides on the IDed nanostructures, whose coding signal then identifies the unique combination, and hence the sequence of the template DNA.

Another aspect of the present disclosure relates to methods of detecting a condition in a sample or a subject, comprising: hybridizing a DNA fragment from the sample or the subject with the composition associated with a nucleic acid, and detecting the presence of double stranded DNA in the IDed nanostructure which indicates the presence of a condition in the sample or subject. In certain embodiments, the nucleic acid comprises a known mutation which is associated with the condition. For example, the presence of the mutation may indicate presence of the condition in the sample or the subject, or vice versa. The nucleic acid can be designed to selectively pair with a DNA containing the mutation but not with a DNA lacking the mutation, under a proper temperature range. When subject to an endonuclease, the unpaired sample DNA lacking the mutation, and also the unpaired nucleic acid on the nanostructure would be digested. Alternatively or additionally, a double stranded DNA dye may be used to detect the presence of the double stranded hybridization product.

Another aspect of the present disclosure relates to methods of detecting a condition in a sample or a subject, comprising: hybridizing a DNA fragment from the sample or the subject with the composition associated with a nucleic acid in a solution, adding a single-stranded endonuclease into the solution, subjecting the solution to a magnetic field, and detecting the presence or coding signal of IDed nanostructure which indicates the presence of a condition in the sample or subject. In certain embodiments, one end of the nucleic acid is associated with a magnetic particle, and the other end of the nucleic acid is associated with an IDed porous nanostructure. The nucleic acid may further comprise a known mutation which is associated with the condition, and can be designed to indicate presence of the mutation in a sample DNA by selectively pairing with the sample DNA with (or without) the mutation. After the hybridization, the endonuclease would digest the unpaired nucleic acid on the IDed nanostructure, thereby separating the magnetic particle and the IDed nanostructure. When subject to a magnetic field, the magnetic particles, associated with or without the nucleic acid on the IDed nanostructure would be separated, and detection of the presence of coding signal of the IDed nanostructure would indicate pairing of the nucleic acid with the sample DNA, and thereby indicating the presence or absence of the mutation and of the condition of concern.

Another aspect of the present disclosure relates to methods of detecting interaction of a nucleic acid with a testing agent, wherein the nucleic acid is associated with a first IDed porous nanostructure nanostructure having a first coding signal, and the testing agent is associated with a second IDed porous nanostructure having a second coding signal. The methods comprise contacting the first IDed porous nanostructure with the second IDed porous nanostructure, and detecting the interaction of the first and the second coding signals. For example, if the nucleic acid binds to the testing agent, then co-localization of the first and the second coding signals can be detected. The testing agent can be any suitable biological or chemical agents, for example, nucleic acids, proteins, peptides, aptamers, chemical compounds, antibodies, and etc. In certain embodiments, the first and the second IDed porous nanostructures are contacted in a solution. In certain embodiments, the methods further comprise assembling the first and the second IDed porous nanostructures from the solution to a surface (e.g. by using a magnetic grid, a magnet, etc.).

In certain embodiments, the nanostructure provided herein can be used in the manufacture of therapeutic or diagnostic compositions.

In certain embodiments, the nanostructure may be used to deliver one or more therapeutic agents. For example, the nanostructure may be used to provide for desired delivery (e.g. targeted delivery) and/or desired release (e.g. extended and/or controlled release) of the therapeutic agent(s). The nanostructure may be delivered to a subject via a suitable route (e.g., intravenous, intraperitoneal, intramuscular, intradermal, subcutaneous, transdermal, subdermal, intracranial, intranasal, mucosal, anal, vaginal, oral, sublingual, buccal, or nasal). The nanostructure suitable for therapeutic use may comprise one or more therapeutic agent, either as an associated payload, or as a conjugated molecule (e.g. a prodrug). Optionally, for target delivery, the nanostructure may further comprise a targeting moiety.

The nanostructure may also be used on samples (e.g. in vitro or ex vivo) for diagnostic use. For example, the nanostructure may be applied to or contacted with a sample under a suitable condition that allows an expected reaction (e.g. hybridization, amplification, affinity binding, staining, etc.) with its target molecule suspected of being present in the sample (e.g. a biomarker for a condition, a marker antigen, a pathogen, and/or a virus gene sequence). The presence and/or extent of the reaction may be detected or measured, so as to provide for information of presence or absence of the target molecule, and/or the amount (e.g. concentration) of such target molecule. The nanostructures useful in such diagnostic use may comprise an agent capable of reacting with the interested target molecule. Such agent can be a binding partner such as antibody, antigen, aptamer, nucleic acid, probe, chemical or other suitable agents. Such agent may be associated with the nanostructure as a payload and/or be conjugated to the nanostructure. Optionally, the nanostructure may further comprise a detectable label that allows detection of the reaction.

In certain embodiments, the nanostructure provided herein can be used in the manufacture of reagents useful in a qualitative or quantitative test. For example, the nanostructure may be used to contact an analyte and to allow identification and/or quantification of the analyte. The analyte may be any substance that can be detected, such as chemicals, explosives (e.g. TNT), drugs (e.g. cocaine, heroin, cannabis, etc.), hazardous substances, metal ions (e.g. heavy metal ions), contaminants, organic compounds, alcohol, anabolic steroids, protons, nitric monoxide, blood sugar, and metabolites etc. The analyte may be in any suitable sample form, such as for example, in a biological specimen (e.g. urine, sweat, breath, hair, saliva, and blood), in an environmental specimen (e.g. river water, soil, and air), or in a lab sample (e.g. dissolved in a lab buffer). The nanostructure suitable for such analytic use may comprise a detecting agent (e.g. as a payload or as a conjugate molecule) that allows identification and/or quantification of the analyte, and such detecting agent can be appropriately selected by people in the art based on the known detection methods for the analyte.

In certain embodiments, the nanostructure provided herein can be used in the manufacture of reagents useful in molecular imaging. For example, the nanostructure provided herein may be administered in vivo or in vitro to a subject (e.g., a mammal, a human or other animals) via a suitable route (e.g. intravenously, intra-arterially, orally, dermal application, subcutaneously, intramuscular, intraperitoneal), followed by image generation of the subject using a suitable device, such as an X-ray device, an MRI device, a CT device, or devices for optical imaging, optical coherence tomography, computed tomography, or positron emission tomography. The generated images may be further analyzed to provide distribution of the administered nanostructures in the subject, or in an interested tissue, organ or compartment of the subject. The nanostructure useful in molecular imaging may carry or be associated with a payload comprising a fluorescent molecule, a bioluminescent molecule, a radio isotope and/or other agents as a suitable imaging or contract agent (A review on molecular imaging can be found at: Weissleder, R. et al, Radiology, 219: 316-333 (2001)).

In certain embodiments, the nanostructure provided herein can be used in the manufacture of reagents useful in separation, purification or enrichment. For example, the nanostructure may be used to contact a mixture which contains a component for which a separation/purification/enrichment is interested. The interested component may be, for example, a cell (e.g. tumor cell, a cell expressing a specific marker antigen), a protein (e.g. antibody, antibody fragment, antigen etc.), a nucleic acid, and a chemical compound etc. The mixture may be or be derived from, for example, a biological specimen (e.g. blood, serum, plasma, urine, tissue, cell extract, cell lysate), a synthesized chemical product, an extract of herbs or plants, and etc. The nanostructure comprises one or more capturing agents that have an affinity to the interested component. For example, the nanostructure may carry or be conjugated with, for example, an antigen, antibody, complementary nucleic acid, aptamer, and any other suitable binding partners. The nanostructure with the interested component captured thereon, may be separated from the remnants of the mixture using any suitable separation methods, such as for example, by filtration, centrifugation, chromatography (e.g. size-exclusion chromatography), application of magnetic field (e.g. for nanostructures comprising magnetic nanoparticles), or application of electrical field. Optionally, the capture of the interested component by the nanostructure is reversible, so that the component may be released from the nanostructure after the separation/purification/enrichment.

In certain embodiments, the nanostructure provided herein can be used in the manufacture of semiconductors. Such semiconductors may be used in light emitting devices, optoelectronic devices, fluorescent label, electrodes, photovoltaic cells, optical sensors, and biosensors etc. Some of these applications are described in detail in Schmid, G. et al., Nanoparticles: From Theory to Application, published by John Wiley & Sons, 2011.

EXAMPLES

Example 1

Preparation of Nanoparticles of Gold and Semiconductor Quantum Dots with the Low Density Siliceous Structure The low density siliceous structure is a versatile and flexible platform for making biocompatible nanoparticles. For example, to incorporate gold nanoparticles into the siliceous structure, Au nanoparticles synthesized in either water solution or organic solutions could be utilized. Briefly, Au was precipitated out at the sample vial bottom after centrifuge at 13 k rpm for 15 min, then silane molecules such as aminopropyltrimethoxysilane and TMAOH was added. The reaction solvent was adjusted using a higher number alcohol, such as butanol or proponol. Then the sample was sonicated for a few hours with constant blowing of air bubbles, afterwards, PEG-silane, mercaptopropyltrimethoxysilane and aminopropyltrimethoxysilane were added, the sample was sonicated for additional 2-3 hours. Afterwards, mixture of chlorotrimethylsilane, methanol, and TMAOH or other silane molecules that only have one alkoxyl group connecting with the silicon atom were added to react with surface siloxyl groups presented on the surface of the already grown siliceous structure. After additional sonicating and aging, stable nanoparticles with the highly porous siliceous structure were collected and stored within physiological buffer solutions through centrifugal filtering, centrifugation, dialysis or any other solution exchange methods. The resulting Au nanostructure was observed under TEM, and an exemplary TEM image was shown in FIG. 2. The nanoparticle core size was about 20 nm and hydrodynamic size was about 60 nm. The siliceous coating was not obvious from the TEM.

Example 2

Preparation of Nanoparticles of Semiconductor Quantum Dots with the Low Density Siliceous Structure As another example, semiconductor quantum dots in the form of individual nanocrystal or nanocrystal clusters could also be incorporated within the highly porous/low density siliceous structure. For example, CdSe/ZnS nanoparticles in organic solvents such as chloroform, Toluene, or Hexane could be precipitated out by adding methanol and then through centrifugation. The nanocrystal pellet was then re-dispersed in aminopropyltrimethoxysilane or mercaptopropyltrimethoxysilane. Afterwards, tetramethyl ammonium hydroxide was added. Then the reaction solvent was adjusted using a higher number alcohol, such as butanol or proponol. After sonicating the sample for 1-4 hours and blowing air bubbles, small amount of aminopropyltrimethoxysilane, mercaptopropyltrimethoxysilane, polyethyleneoxidesilane and water was subsequently added, and the sample then underwent sonication for another 1 to 4 hours. Then, mixture of chlorotrimethylsilane, methanol, and TMAOH or other silane molecules that only have one alkoxyl group connecting with the silicon atom were added. This sample was then sonicated for another 1-4 hours, followed by overnight aging under mild shaking or vibration. The resulting nanoparticles with low density/highly porous siliceous structure were transferred into physiological buffer solutions by centrifugal filtering, centrifugation, dialysis or any other solution exchange methods. The resulting CdSe/ZnS nanostructure was observed under TEM, and an exemplary TEM image was shown in FIG. 3. The nanoparticle core size was about 10 nm and hydrodynamic size was about 200 nm. The siliceous coating was not obvious from the TEM.

Example 3

Preparation and Characterization of Low Density Magnetic Particles

Preparation of the Magnetic Porous Nanostructure:
Magnetic particles formed by clustering multiple small particles and then being coated were prepared. The clustering happened with the addition of a worse solvent for generating dispersed nanoparticles, such as butanol or isopropanol, followed by the addition of the silanization reagents to form the nanostructure under constant blowing of air bubbles. The magnetic nanostructure as prepared were observed under TEM (FIG. 5). As shown in FIG. 5, each large core nanoparticle comprised a cluster of small nanoparticles, and the coating was substantially invisible under TEM.

Characterization of Density of the Coating:
To calculate the density of the coating, both the dry mass and the volume of the coating were characterized.

Since the magnetic particles had high magnetic response that they could be directly captured using a magnet. This allowed generation of dry particles to measure the mass of the material. The dry mass of particles before and after coating was quantified as follows. 200 ul of the coated particle solution was pipetted out into a centrifugal vial whose mass was pre-measured. Coated magnetic nanoparticles were captured to the side of the vial wall, and the supernatant was removed. The captured particles were washed with water. At the end, the particles absorbed to the side wall were left to dry in the open vial under a fume hood. The mass of the vial with the dry coated particles were measured. The dry coated particle mass was calculated by subtraction of the mass of the vial from the mass of the vial with the dry coated particles inside. To measure the mass of the particles before coating, uncoated particles corresponding to the same amount of the magnetic material as in the coated nanoparticles, assuming an 80% coating processing yield, was captured to the side of the vial, and dried. The dry mass of the particles before coating was measured by subtraction of the mass of the vial from the mass of the vial with the dry uncoated particles inside. The mass of the coating was equal to the mass of the dry coated particles minus the dry mass of particles before coating.

TABLE 1

| Average Core mass (n = 3) | 0.67 mg |
| Average Coating mass (n = 3) | 0.06 mg |

The total volume of the coating was calculated using the number of large particles in the above mass multiplied by the volume of the coating of each individual large nanoparticles. The particles were suspended in an aqueous solution, and the volume of the coating of each large particle was calculated as $4/3 \times \pi (R^3_{with\ coating} - R^3_{core})$, in which the $R_{with\ coating}$ of an individual large nanoparticle was measured using core with coating dynamic light scattering (DLS) technique, and the $R_{core}$ of the large core particle was directly imaged and measured using TEM (see FIG. 5).

TABLE 2

| | |
|---|---|
| Average size of large core nanoparticles under TEM | 210 nm |
| Average size of coated large nanoparticles under DLS | 217-357 nm |
| Average coating volume of an coated large nanoparticle | $4/3 \times \pi\,(110^3 - 105^3)$ nm$^3$ |

The number of large particles in the mass was calculated by dividing the total number of small nanoparticles by the number of small nanoparticles in each large nanoparticle. The total number of small nanoparticles was estimated by dividing the mass of total magnetic material by the mass of an individual small nanoparticle (i.e. calculated using the size and density of the small nanoparticle). The number of small nanoparticles in each individual large particle was counted from the TEM micrograph. Hence, the total volume of the coating can be calculated as the volume of coating of a large nanoparticle multiplied by the total number of the large nanoparticles.

TABLE 3

| | |
|---|---|
| Core mass | 0.67 mg |
| Density of core | 5.2 kg/m$^3$ |
| Small nanoparticle size | 16 nm |
| Small nanoparticle Volume | $2.1 \times 10^{-24}$ m$^3$ |
| Mass of each small narnoparticle | $1.1 \times 10^{-17}$ mg |
| Number of small particles in the core | $6.1 \times 10^{16}$ |
| Average number of small particle per large particle | 236 |
| Number of large particles in the core | $2.6 \times 10^{14}$ |
| Total volume of the coating | $4/3 \times \pi\,(110^3 - 105^3)$ nm$^3 \times 2.6 \times 10^{14}$ = $0.1875 \times 10^{-6}$ m$^3$. |

The density of the coating was calculated using the mass of the coating divided by the total volume of the coating, i.e., 0.06 mg/0.1875×10$^{-6}$ m$^3$=0.32 mg/cm$^3$.

The density of the low density siliceous structure prepared herein is only 0.32 mg/cm$^3$, which is significantly lower than the density of some reported silica coatings, for example, those reported in Vincent et al (Vincent, A. et al, J. Phys. Chem. C 2007, 111, 8291-8298), that have a density of 1-2 g/cc and are 10$^4$ denser than the siliceous structure provided herein.

Characterization of Porosity Using BET Method:

Large magnetic nanoparticles after coating were captured to the side of the vial and dried. 2 samples of 65 mg (sample 1) and 45 mg (sample 2) dry mass were prepared for the BET measurement.

Surface pore sizes were measured using BET method for the dry mass of the coated nanoparticles. The results are shown in the below Tables.

TABLE 4

Characterization for Sample 1

| | |
|---|---|
| Surface Area | 14.166 m$^2$/g |
| Total pore volume for pores smaller than 677.5 Å (Radius) at P/P$_0$ = 0.98562 | $7.562 \times 10^{-2}$ cc/g |

TABLE 5

Characterization for Sample 2

| | |
|---|---|
| Surface Area | 6.380 m$^2$/g |
| Total pore volume for pores smaller than 683.3 Å (Radius) at P/Po = 0.98575 | $7.099 \times 10^{-2}$ cc/g |

The surface area and the pore volume of the porous nanostructure were measured with dry mass of the porous nanostructure. If measured with a nanostructure sample suspended in an aqueous solution, the pore volume and the surface area are expected to be much higher than the measurements with the dry mass, as the density of the coating has been shown to be at least 10$^4$ lower than those reported in the art.

The measured density based on the dry power samples does not reflect the real density of the 3-D structure because of the ultralow density of the 3-D structure, the framework easily collapses during the drying process, hence providing much smaller numbers in the porosity measurement than when the 3-D structure is fully extended, for example, like when the porous nanostructure is fully extended in a buffer solution.

Example 4

Preparation and Characterization of IDed Nanostructure.

Preparation of IDed Magnetic Nanostructure.

The IDed fluorescent magnetic nanoparticles were prepared by incorporating both magnetic nanoparticles and fluorescent particles, such as organic fluorophores or organically soluble quantum dots into the porous nanostructure formulation process, where each individual component, i.e., magnetic or fluorescent was associated with the porous matrix through covalent binding or non-covalent interaction, such as metal-ligand chelating, hydrophobic or electrostatic association. The different IDed nanostructures were dispersed in a buffer, and an image under fluorescent microscope showed the different colors of the IDed nanostructures (see FIG. 9).

Conjugation of the IDed Nanostructures.

The IDed nanostructures were first conjugated with streptavidin through covalent binding of amine groups of streptavidin to mercapto groups on the surface of IDed nanostructures. After streptavidin conjugation, each type of the IDed magnetic nanostructures was magnetically purified, and redispersed in a separate buffer solution.

A sense DNA strand and its antisense DNA strand, both biotinylated, were commercially obtained. To allow conjugation of the IDed nanostructure to the corresponding biotinylated DNA, the red IDed nanostructure was mixed with biotin-sense DNA, and the green IDed nanostructure was mixed with biotin-antisense DNA. The ratio of biotin-DNA to the IDed nanostructures could be ranged from 1 to 100. The conjugation were performed under room temperature in an appropriate buffer under continuous rotating, and incubated for 1 to 4 hours. Each of the IDed nanostructure-DNA conjugates was purified using a magnet, and washed once with buffer. Afterwards, the IDed nanostructure-sense DNA and IDed nanostructure-antisense DNA were mixed together for the hybridization reaction, and left on a rotator overnight.

Figure 11:
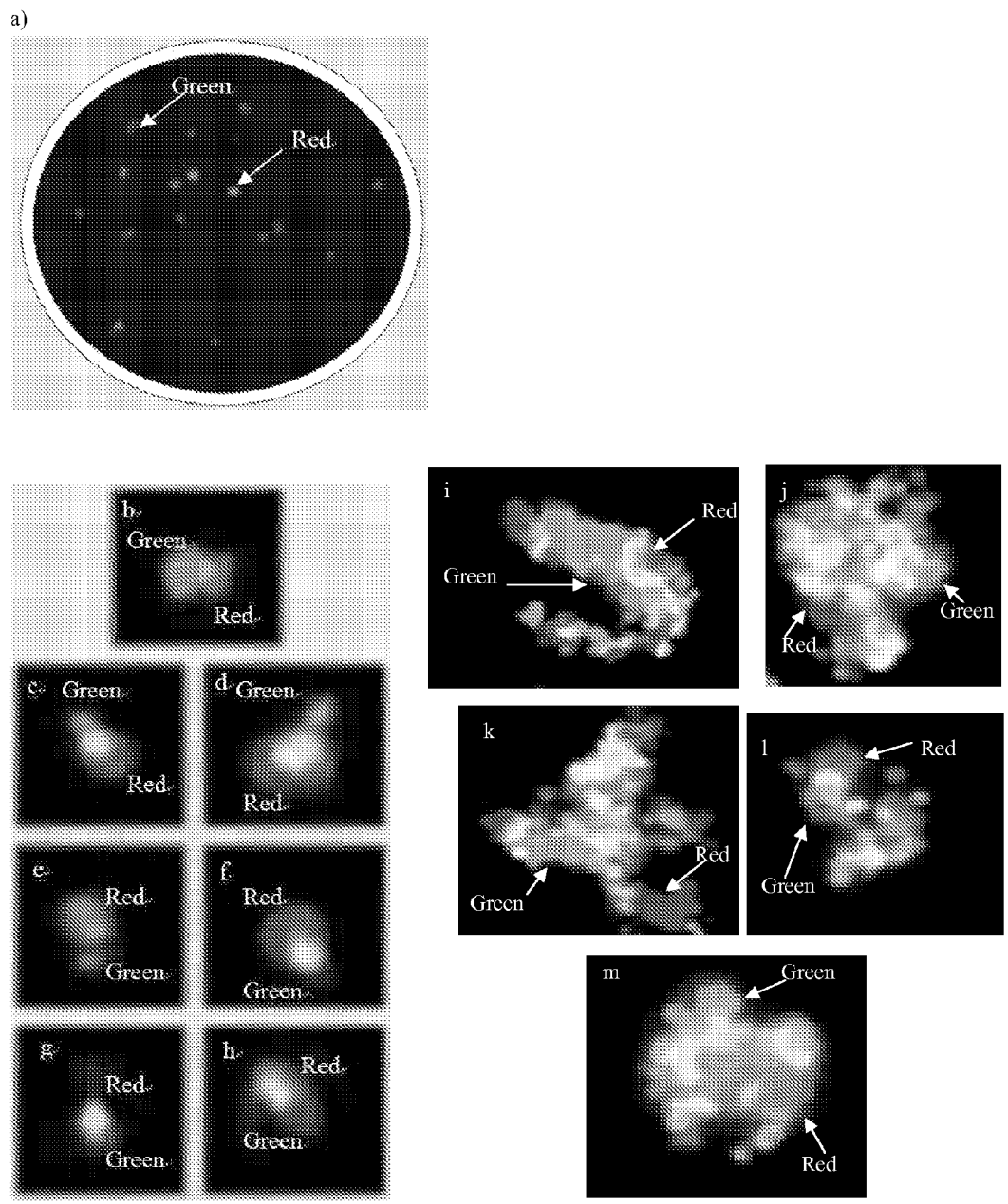
FIG. 11. DNA hybridization results using IDed nanostructures. (a) Image of control experiment: mixture of red and green IDed nanostructures without DNA oligomers. (b)-(m) DNA hybridization results: red and green IDed nanostructures were conjugated respectively with complementary DNA oligomeric strands, and successful hybridization was manifested by the association of red and green IDed nano structures.

On the second day, an aliquot of solution was taken out of the hybridization solution and observed under microscope. Images from the hybridized sample solution were compared with images from the control sample, where the same quantity of the same two types of IDed nanoparticle-streptavidin conjugates without DNA oligomer were mixed together and incubated overnight. Results were shown in FIG. 11(a) (control sample), and FIG. 11(b)-(m) (DNA hybridization sample). As shown in the results, DNA hybridization was manifested as co-localization of both the red and green IDed nanostructures.

A magnetic grid can also be used to facilitate the detection. After hybridization of the IDed nanostructure-sense DNA and IDed nanostructure-antisense DNA, a magnetic grid was placed onto a surface of a flow cell, the hybridization sample was allowed to flow through the surface of the magnetic grid, and captured by the magnetic grid. This method allowed the hybridization reaction to happen in a solution, while the detection can be conducted on a surface. Images from the hybridized sample solution were compared with images from the control sample with the magnetic grid. Results were shown in FIG. 12(a) (control sample) and FIG. 12(b) (DNA hybridization sample). As shown in the results, DNA hybridization was manifested as co-localization of both the red and green IDed nanostructures on the magnetic grid. No obvious co-localization of the two IDed nanostructures was observed.

What is claimed is:

1. A method of detecting a condition in a sample or a subject, comprising:
   providing a composition comprising
   (i) an IDed porous nanostructure wherein the IDed porous nanostructure is associated with a known code or a known label that allows identification of the IDed porous nanostructure, and
   (ii) a single stranded nucleic acid,
   wherein the single stranded nucleic acid is associated with the IDed porous nanostructure, and wherein the IDed porous nanostructure comprises at least one core nanoparticle coated with a low density porous 3-D structure having a density of <1.0 g/cc, and the density is determined using the dry mass of the 3-D structure divided by the total volume of the 3-D structure in an aqueous solution;
   hybridizing DNA fragments from the sample or the subject with the composition such that at least some of the DNA fragments from the sample or the subject are paired with the single stranded nucleic acid to form double stranded DNA;
   treating the composition with a single stranded DNA endonuclease such that unpaired single stranded nucleic acids are digested; and
   detecting the stranded DNA associated with the IDed porous nanostructure, which indicates the presence of the condition in the sample or subject.

2. The method of claim 1, wherein the single stranded nucleic acid comprises a known mutation associated with the condition.

3. The method of claim 1, wherein the detecting step comprises treating the hybridization product with a double stranded DNA dye.

4. The method of claim 1, further comprising assembling a plurality of IDed nanostructures from a solution onto a surface before detecting the double stranded DNA.

5. The method of claim 4, wherein the assembling is based on chemical interaction.

6. The method of claim 4, wherein the IDed porous nanostructure is magnetic.

7. The method of claim 6, wherein the assembling is based on magnetic interaction.

8. The method of claim 7, wherein the IDed porous nanostructures are assembled in an ordered array format in the presence of an applied magnetic field.

9. The method of claim 1, wherein the IDed porous nanostructure is magnetic.

10. A method of detecting a condition in a sample or a subject, comprising:
    providing a composition comprising
    (i) an IDed porous nanostructure having a coding signal,
    (ii) a single stranded nucleic acid, and
    (iii) a magnetic particle,
    wherein the magnetic particle is associated with one end of the single stranded nucleic acid and the IDed porous nanostructure is associated with the opposite end of the single stranded nucleic acid, wherein the IDed porous nanostructure comprises at least one core nanoparticle coated with a low density porous 3-D structure having a density of <1.0 g/cc, and the density is determined using the dry mass of the 3-D structure divided by the total volume of the 3-D structure in an aqueous solution;
    hybridizing DNA fragments from the sample or the subject with the composition in a solution such that at least some of the DNA fragments from the sample or the subject are paired with the single stranded nucleic acid to form double stranded DNA;
    adding a single-stranded endonuclease into the solution;
    subjecting the solution to a magnetic field, thereby collecting the magnetic particles associated with or without the single stranded nucleic acid; and
    detecting the presence of the coding signal of the IDed porous nanostructure, which indicates the presence of the condition in the sample or subject.

11. The method of claim 10, wherein the single stranded nucleic acid in the composition comprises a known mutation associated with the condition.

12. A method of detecting coding signals of a plurality of IDed nanostructures in a solution simultaneously without a need for a substrate, comprising
    passing a light from a solution comprising the plurality of IDed nanostructures through a microlens array to a photosensor array; and
    processing the light data to identify each IDed nanostructure in the solution, wherein the IDed nanostructure comprises at least one core nanoparticle coated with a low density porous 3-D structure having a density of <1.0 g/cc, and the density is determined using the dry mass of the 3-D structure divided by the total volume of the 3-D structure in an aqueous solution.

* * * * *